(12) United States Patent
Heirman et al.

(10) Patent No.: US 10,159,755 B2
(45) Date of Patent: Dec. 25, 2018

(54) RNA TRANSCRIPTION VECTOR AND USES THEREOF

(71) Applicant: Vrije Universiteit Brussel, Brussels (BE)

(72) Inventors: Carlo Heirman, Dendermonde (BE); Kristiaan Thielemans, Antwerpen (BE)

(73) Assignee: Vrije Universiteit Brussel, Brussels (BE)

( * ) Notice: Subject to any disclaimer, the term of this patent is extended or adjusted under 35 U.S.C. 154(b) by 0 days.

(21) Appl. No.: 15/034,048

(22) PCT Filed: Nov. 12, 2014

(86) PCT No.: PCT/EP2014/074349
§ 371 (c)(1),
(2) Date: May 3, 2016

(87) PCT Pub. No.: WO2015/071295
PCT Pub. Date: May 21, 2015

(65) Prior Publication Data
US 2016/0279266 A1   Sep. 29, 2016

(30) Foreign Application Priority Data
Nov. 12, 2013 (EP) .................................. 13192555

(51) Int. Cl.
| | |
|---|---|
| *A61K 48/00* | (2006.01) |
| *A61K 31/7105* | (2006.01) |
| *C12N 15/85* | (2006.01) |
| *A61K 39/00* | (2006.01) |
| *C07K 14/705* | (2006.01) |

(52) U.S. Cl.
CPC ...... *A61K 48/0066* (2013.01); *A61K 31/7105* (2013.01); *A61K 39/0011* (2013.01); *C07K 14/70575* (2013.01); *C07K 14/70596* (2013.01); *C12N 15/85* (2013.01); *A61K 2039/53* (2013.01); *A61K 2039/54* (2013.01); *A61K 2039/55516* (2013.01); *C12N 2320/52* (2013.01); *C12N 2810/10* (2013.01); *C12N 2830/50* (2013.01); *C12N 2840/105* (2013.01)

(58) Field of Classification Search
CPC .............................................. A61K 48/0066
See application file for complete search history.

(56) References Cited

U.S. PATENT DOCUMENTS

| | | | |
|---|---|---|---|
| 7,608,699 B2 * | 10/2009 | Muesing | C07K 14/005 |
| | | | 536/23.1 |
| 2004/0043468 A1 | 3/2004 | Mauro et al. | |

FOREIGN PATENT DOCUMENTS

| | | | | |
|---|---|---|---|---|
| JP | 2007295846 A | | 11/2007 | |
| WO | WO 97/31932 | * | 9/1997 | ............. C07H 21/04 |
| WO | WO0155369 A1 | | 8/2001 | |
| WO | WO 2005/117989 | * | 12/2005 | ............. A61K 48/00 |
| WO | WO2009034172 A1 | | 3/2009 | |
| WO | WO2009075886 A1 | | 6/2009 | |

OTHER PUBLICATIONS

Conrad et al. (2005, EMBO J., vol. 24(10), pp. 1831-1841).*
Conrad et al, "A Kaposi's sarcoma virus RNA element that increases the nuclear abundance of intronless transcripts", The EMBO Journal, vol. 24, No. 10, May 18, 2005, pp. 1831-1841, XP055111814, ISSN: 0261-4189, DOI: 10.1038/sj.emboj.760066.
Kazimierz et al, "Conservation of a Triple-Helix-Forming RNA Stability Element in Noncoding and Genomic RNAs of Diverse Viruses", Cell Reports, vol. 2, No. 1, Jul. 26, 2012, pp. 26-32, XP055111571, ISSN: 2211-1247, DOI:10.1016/j.celrep.2012.05.020.
Pawlicki et al, "Primary microRNA transcript retention at sites of transcription leads to enhanced microRNA production", Microbiology and Molecular Biology Reviews, vol. 63, No. 2, Jul. 7, 2008, pp. 405-476, XP055111700, ISSN: 1092-2172, DOI: 10.1128/JV.
Massimelli et al: "Stability of a Long Noncoding Viral RNA Depends on a 9-nt Core Element at the RNA 5' End to Interact with Viral ORF57 and Cellular PABPC1", International Journal df Biological Sciences, vol. 7, No. 8, Oct. 16, 2011, pp. 1145-1160, XP055111577, ISSN: 1449-2288, DOI: 1D.7150/ijbs.7.1145.
Jaleco et al, "Genetic modification of human B-cell development: B-cell development is inhibited by the dominant negative helix loop helix factor Id3", Blood, American Society of Hematology, US, vol. 94, No. 8, Oct. 15, 1999, pp. 2637-2646, XP009133172, ISSN: 0006-4971.
Database Geneseq [Online], Jan. 24, 2008, "Gtx IRES DNA sequence PCR primer SEQ ID No. 31.", XP002722821, retrieved from EBI accession No. GSN:ANZ24567, Database accession No. ANZ24567 sequence.
Hu et al, "rRNA—complementarity in the 5' untranslated region of mRNA specifying the Gtx homeodomain protein: Evidence that base-pairing to 18S rRNA affects translational efficiency", Proceedings of the National. Academy of Sciences, vol. 96, No. 4, Feb. 16, 1999, pp. 1339-1344, XP055111718, ISSN: 0027-8424, DOI: 10.1073/pnas.96.4.1339.
Van Lint Sandra, Goyvaerts Clea, Maenhout Sarah, et al.—Preclinical Evaluation of TriMix and Antigen mRNA-Based Antitumor Therapy—Cancer Res 2012;72:1661-1671.
Bonehill A, Tuyaerts S, Van Nuffel AM, Heirman C, Bos TJ, Fostier K, Neyns B, Thielemans K—Enhancing the T-cell stimulatory capacity of human dendritic cells by co-electroporation with CD4OL, CD10 and constitutively active TLR4 encoding mRNA.—Mol Ther. Jun. 2008; 16(6)1170-80.

(Continued)

*Primary Examiner* — Thaian N Ton
*Assistant Examiner* — David A. Montanari
(74) *Attorney, Agent, or Firm* — Dinsmore & Shohl LLP

(57) ABSTRACT

The present invention relates to an improved RNA transcription vector, which is very suitable for the production of mRNA for in vivo therapeutic purposes. The improvements in the vector reside in the presence of a translation enhancer (TE) and a nuclear retention element (NRS), especially when the latter is the "Expression and Nuclear Retention Element" (ENE) of Kaposi's sarcoma associated Herpes virus (KSHV).

5 Claims, 13 Drawing Sheets
Specification includes a Sequence Listing.

(56) References Cited

OTHER PUBLICATIONS

International Search Report and Written Opinion completed Feb. 4, 2015, pertaining to PCT/EP2014/074349 filed Nov. 12, 2014.
European Search Report completed Apr. 4, 2014, pertaining to EP13192555.4-1406 filed Nov. 12, 2013.
Jul. 5, 2012 (Jul. 5, 2012), XP002722820, Retrieved from the Internet: URL:http://www.sciencedirect.com/science/article/pii/S2211124712001593/pdfft?md5.cb6 cc4b5af2540243b6346608a45bccb&pid=1-s2.0-S 2211124712001593-main.pdf.

* cited by examiner

Treated tumor

Treated tumor

Contralateral
Non-treated tumor

Contralateral
Non-treated tumor

- Treated tumor Control mRNA
- Non-treated tumor Control mRNA
- Treated tumor TriMix mRNA
- Non-treated tumor TriMix mRNA Treated tumor Treated tumor Contralateral Non-treated tumor Contralateral Non-treated tumor

- Treated tumor Vehicle
- Non-treated tumor Vehicle
- Treated tumor Control mRNA
- non-treated tumor Control mRNA
- Treated tumor TriMix mRNA
- Non-treated tumor TriMix mRNA

RNA TRANSCRIPTION VECTOR AND USES THEREOF

FIELD OF THE INVENTION

The present invention in general relates to an improved RNA transcription vector, which is very suitable for the production of mRNA for in vivo therapeutic purposes. The improvements in the vector in particular reside in the presence of a translation enhancer and a nuclear retention element.

BACKGROUND TO THE INVENTION

Although our immune system is capable of discriminating healthy cells from tumor cells and infectious agents, it sometimes fails in appropriately recognising and reacting to the problem. Therefore, medical science has focused on the development of several strategies that aid the immune system in the surveillance and elimination of tumor cells and infectious agents. Dendritic cells (DCs) are antigen-presenting cells (APCs) which are known as key players in the instigation of immune responses and much effort has been put in the exploitation of DCs in immunotherapy. In the case of cancer for example, the aim is the induction and perpetuation of a tumor specific immune response by eliciting effector T cells that can specifically decrease tumor load and induce immunological memory to control tumor relapse. Once targetable tumor associated antigens (TAA) have been identified, they can be used to load the professional APCs, i.e. the dendritic cells, either in vivo or ex vivo.

Different antigen formats have been assessed with regards to DC for in vivo or ex vivo immunotherapy such as peptides, proteins, whole tumor cell extracts, plasmid DNA or mRNA. Among these approaches, antigen-encoding mRNA is emerging as particularly promising. The advantage over the classical vaccination with peptides is that mRNA encodes the genetic information for the whole antigen. The full-length antigen is processed and all available epitopes are presented in the MHC molecules of the patient, without the need to determine HLA specific peptides. No patients need to be excluded from the treatment because the available peptides do not match their HLA type. In addition, mRNA does not pose the risk of genomic integration giving it a favourable safety profile compared to DNA or viral vectors. Due to its transient nature, mRNA is only expressed during a short period of time and is eventually degraded into natural products. Furthermore, mRNA acts as its own adjuvant, prompting co-stimulatory signals, which is advantageous in the context of mRNA-based immunotherapy. Two routes for exogenous mRNA delivery into DCs have been applied: either ex vivo with subsequent adoptive transfer of transfected DCs or by direct administration of mRNA and uptake in vivo.

A study performed by Diken et al. (2011) highlights that the maturation stimulus and/or timing of its delivery have to be selected carefully as the uptake of mRNA is dependent on macropinocytosis, a function of immature DCs that is lost upon DC maturation. Consequently, co-delivery of classical maturation stimuli, such as lipopolysaccharide (LPS), with TAA mRNA has a negative impact on the bioavailability of the antigen, a parameter that co-determines the induction of antigen-specific T cell responses (Van Lint 2012; Diken 2011). To date two different strategies have been explored to simultaneously load the DCs with TAA mRNA and activate them in vivo.

Fotin-Mleczek et al. (2011) described a two-component system containing free- and protamin-complexed mRNA, providing an antigen source for adaptive immunity together with enhanced triggering of the pathogen recognition receptor, TLR7. This immunization strategy resulted in the induction of a strong anti-tumor immune response and in sustained memory responses, which is important, as memory T cells should avoid tumor re-appearance.

Bonehill et al., 2008 evaluated the use of specific combinations of mRNA for adjuvant purposes, initially for the activation of ex vivo generated DCs but equally applicable for direct administration and uptake in vivo (Bonehill, 2008). This has lead to a patent application (WO2009034172) in which the inventors describe that the T cell stimulatory capacity of antigenic-peptide pulsed antigen presenting cells or antigen presenting cells (co-) electroporated with an mRNA encoding a TAA can be greatly enhanced by providing them with different molecular adjuvants through electroporation with a mixture of mRNA or DNA molecules encoding two or more immunostimulatory factors. Proof of concept is provided that such modified antigen presenting cells pulsed with a target-specific peptide or co-electroporated with mRNA encoding a target-specific antigen can stimulate antigen-specific T cells both in vitro and after vaccination and thus form a promising new approach for anti-tumor, anti-viral, anti-bacterial or anti-fungal immunotherapy. A preferred combination of immunostimulatory factors used in the invention is CD40L and caTLR4, or CD40L and CD70. In other preferred embodiments, the combination of CD40L, CD70 and caTLR4 immunostimulatory molecules is used, which is called "TriMix" hereinafter.

The present invention relates to an RNA transcription vector containing a 5' translation enhancer sequence and a 3' nuclear retention sequence. The vector according to the present invention, shows an unexpected improvement in expression of the proteins encoded by the in vitro transcribed mRNA in comparison with an empty pUC vector, or with vectors that contain either a translation enhancer or a nuclear retention sequence. These improvements are in particular due to the simultaneous presence of the two components: a translation enhancer and a RNA stabilizing sequence in the vector, and the incorporation thereof in the thus obtained expression product. Furthermore, in vivo application of TriMix mRNA obtained from the vector of the present invention in a mouse cancer model results in a slower growth of tumors and an increased life expectancy of said mice.

SUMMARY OF THE INVENTION

In a first aspect the present invention provides a nucleic acid vector comprising a translation enhancer (TE) sequence having at least 80% sequence identity to SEQ ID No1, a transcribable nucleic acid sequence and a nuclear retention sequence represented by SEQ ID No4.

In a specific embodiment, the transcribable nucleic acid sequence is selected from the list comprising mRNA encoding CD40L, CD70, caTLR4 or antigen/disease specific mRNA.

In a preferred embodiment, the translation enhancer is represented by anyone of SEQ ID No1, 2, or 3, more in particular SEQ ID No 1.

In a further aspect, the present invention provides a method of increasing stability and/or translation efficiency of in vitro transcribed RNA; said method comprising the steps of:

(i) providing a vector according to this invention, wherein said transcribable nucleic acid sequence is a transcribable DNA sequence, which corresponds to said RNA to be transcribed; and (ii) transcribing in vitro the transcribable DNA sequence;

In yet a further embodiment, the present invention provides an RNA molecule comprising a translation enhancer (TE) having at least 80% sequence identity to SEQ ID No1, a transcribable nucleic acid sequence, and a nuclear retention sequence represented by SEQ ID No4.

Said RNA molecule may further comprise a poly-A tail.

In the context of the RNA molecules of the present invention, said translatable nucleic acid sequence may be selected from the list comprising mRNA encoding CD40L. CD70, caTLR4 or antigen/disease specific mRNA.

In a preferred embodiment of the RNA molecules, the translation enhancer is represented by any one of SEQ ID No 1, 2 or 3; more in particular SEQ ID No1.

The present invention further provides a composition comprising one or more RNA molecules according to this invention; more in particular said one or more RNA molecules represent mRNA molecules which encode CD40L, CD70 and caTLR4.

The composition according to the present invention, may further comprise mRNA encoding antigen/disease specific mRNA.

The present invention further provides the use of the RNA molecule(s) and/or composition(s) comprising one or more of said RNA molecules for multiple purposes, such as for example for in vivo or in vitro introduction in a host cell; or for use in medicine.

It is also an aspect of the present invention to provide a kit comprising one or more vectors; one or more RNA molecules; or a composition according to the present invention.

The present invention also provides a method for treating a patient in need thereof with one or more RNA molecules or a composition according to the present invention; wherein said RNA molecules can be administered simultaneously or sequentially with intervals.

The RNA molecules or compositions according to the present invention may be administered to a patient in need thereof by any suitable administration route such as for example intranodal, intradermal, intralymphatic and intratumoral. Furthermore, when treating for example cancer patients, the administration of the RNA molecules or compositions according to the present invention may be used in combination with methods for releasing tumor mRNA from the tumor in the patient, such as for example ablation or sonoporation.

NUMBERED STATEMENTS OF THE INVENTION

1. A nucleic acid vector comprising a translation enhancer (TE) sequence having at least 80% sequence identity to SEQ ID No1, a transcribable nucleic acid sequence and a nuclear retention sequence represented by SEQ ID No4.
2. The nucleic acid vector according to claim 1, wherein said transcribable nucleic acid sequence is selected from the list comprising mRNA encoding CD40L. CD70, caTLR4 or antigen/disease specific mRNA.
3. The nucleic acid vector according to anyone of claims 1-2, wherein said translation enhancer is represented by anyone of SEQ ID No 1, 2 or 3; more in particular SEQ ID No 1.
4. A method of increasing stability and/or translation efficiency of in vitro transcribed RNA; said method comprising the steps of:
   (i) providing a vector according to anyone of claims 1-3, wherein said transcribable nucleic acid sequence is a transcribable DNA sequence, which corresponds to said RNA to be transcribed; and
   (ii) transcribing in vitro said transcribable DNA sequence.
5. An RNA molecule comprising a translation enhancer (TE) having at least 80% sequence identity to SEQ ID No1, a transcribable nucleic acid sequence, and a nuclear retention sequence represented by SEQ ID No4.
6. An RNA molecule according to claim 5 further comprising a poly-A tail.
7. An RNA molecule according to anyone of claim 5 or 6, wherein said transcribable nucleic acid sequence is selected from the list comprising mRNA encoding CD40L. CD70, caTLR4 or antigen/disease specific mRNA.
8. An RNA molecule according to anyone of claims 5-7, wherein said translation enhancer is represented by SEQ ID No 1.
9. A composition comprising one or more RNA molecules as claimed in anyone of claims 5-8.
10. The composition according to claim 9, wherein said one or more RNA molecules represent mRNA molecules which encode CD40L, CD70 and caTLR4.
11. The composition according to claim 10 further comprising mRNA encoding antigen/disease specific mRNA.
12. The use of an RNA molecule according to anyone of claims 5-8, or the composition according to anyone of claims 9-11 for introduction in a host cell.
13. An RNA molecule according to anyone of claims 5-8 or a composition according to anyone of claims 9-11 for use in medicine.
14. A kit comprising one or more vectors according to anyone of claims 1-3; one or more RNA molecules according to anyone of claims 5-8; or a composition according to anyone of claims 9-11.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

Data are presented as mean±SEM. (Paired t test, *P<0.05; P<0.01; *P<0.001). N=6

Figure 2A:
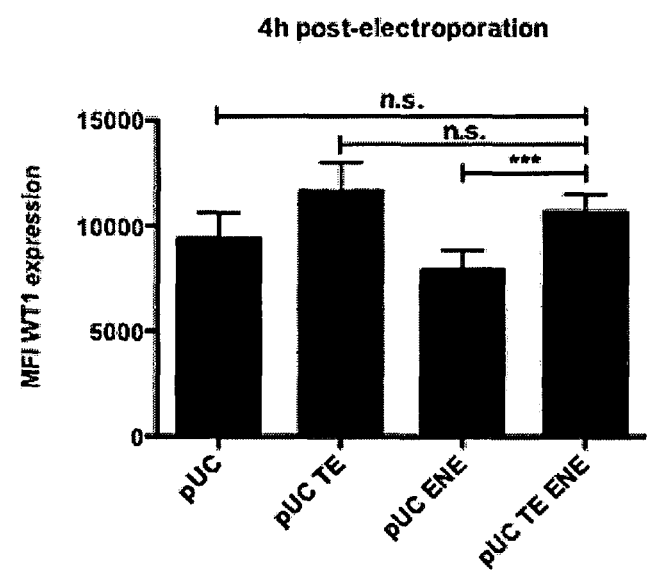
FIG. 2A: WT1 expression in DCs electroporated with WT1 mRNA. iDCs were electroporated with WT1 mRNA encoded by the different vectors and analyzed for their WT1 expression by intracellular staining 4 h post-electroporation. A comparison of MFI values after electroporation of the iDCs with the different WT1-encoding vectors is shown.
Figure 2B:
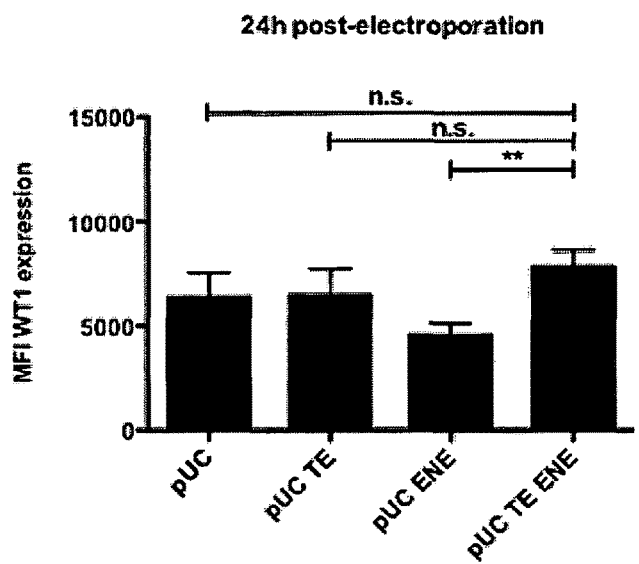

FIG. 2B: WT1 expression in DCs electroporated with WT1 mRNA. iDCs were electroporated with WT1 mRNA encoded by the different vectors and analyzed for their WT1 expression by intracellular staining 24 h post-electroporation. A comparison of MFI values after electroporation of the iDCs with the different WT1-encoding vectors is shown. Data are presented as mean±SEM. (Paired t test, *P<0.05; P<0.01; *P<0.001). N=6

Figure 2C:
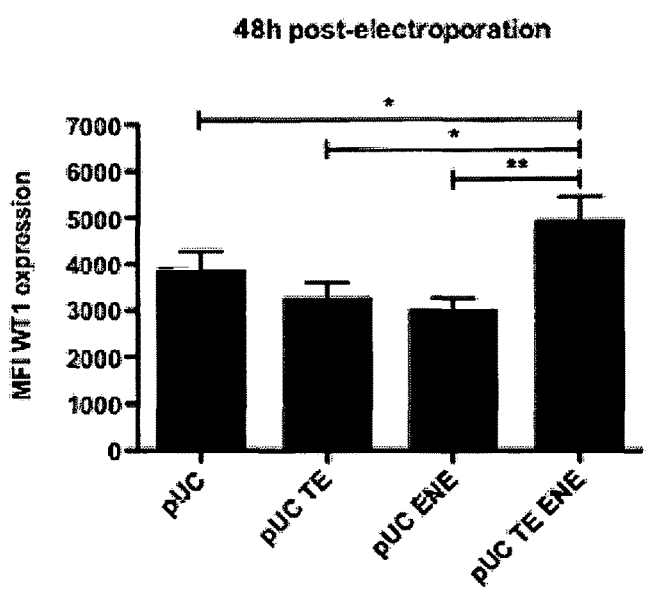

FIG. 2C: WT1 expression in DCs electroporated with WT1 mRNA. iDCs were electroporated with WT1 mRNA encoded by the different vectors and analyzed for their WT1 expression by intracellular staining 48 h post-electroporation. A comparison of MFI values after electroporation of the iDCs with the different WT1-encoding vectors is shown. Data are presented as mean±SEM. (Paired t test, *P<0.05; P<0.01; *P<0.001). N=6

Figure 3:
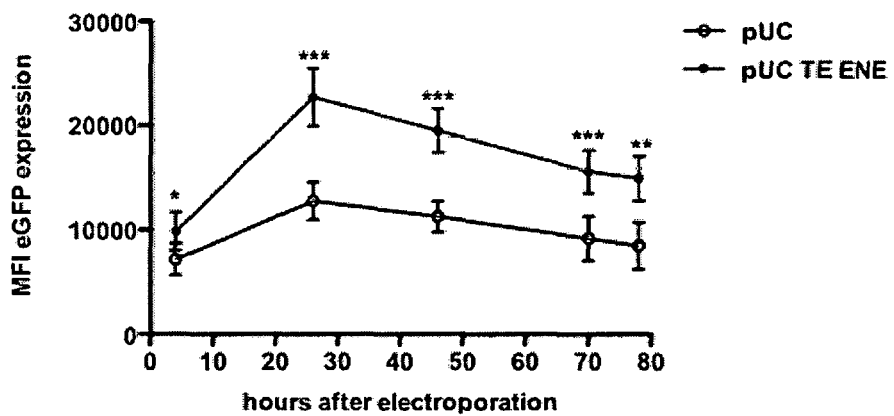

FIG. 3: Kinetics of eGFP expression of DCs. iDCs were co-electroporated with eGFP and TriMix mRNA encoded by the pUC-vector or the pUC TE ENE-vector. eGFP expression was analyzed at several time points post-electroporation. The MFI value of the eGFP positive DC population was analyzed. Data are presented as mean ±SEM. (Paired t test, *P<0.05; P<0.01; *P<0.001). N=9

Figure 4A:
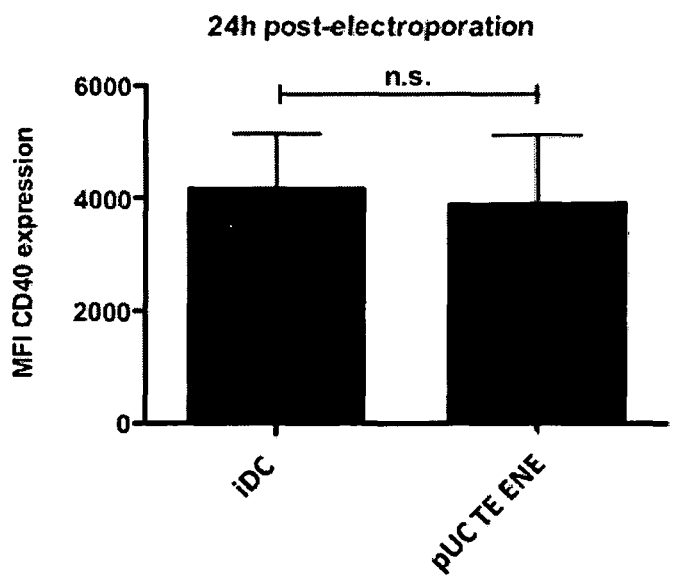

FIG. 4A: Phenotype of immature and mature DCs. MFI values of the indicated molecules were investigated 24h post-electroporation of iDCs. Data are represented as mean ±SEM. (Paired t test, *P<0.05; P<0.01; *P<0.001). CD40 N=9; CD70 N=19; CD80 N=12; CD 83 N=12; CCR7 N=12.

Figure 4B:
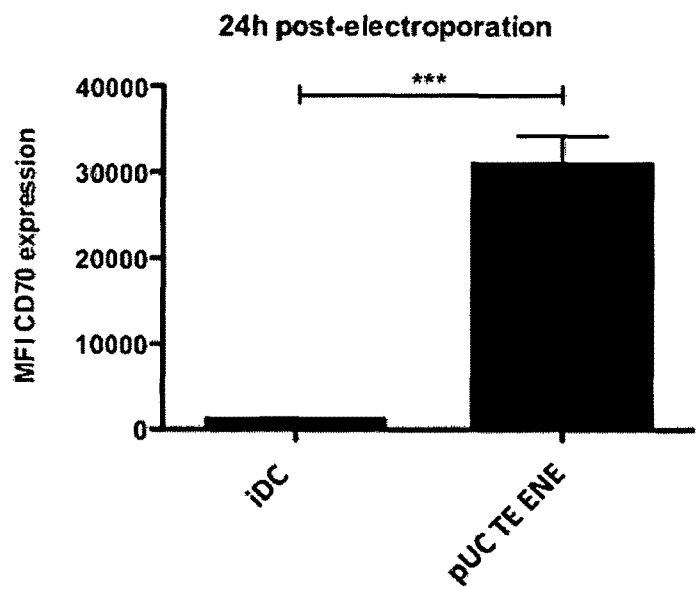

FIG. 4B: Phenotype of immature and mature DCs. MFI values of the indicated molecules were investigated 24h post-electroporation of iDCs. Data are represented as mean ±SEM. (Paired t test, *P<0.05; P<0.01; *P<0.001). CD40 N=9; CD70 N=19; CD80 N=12; CD 83 N=12; CCR7 N=12.

Figure 4C:
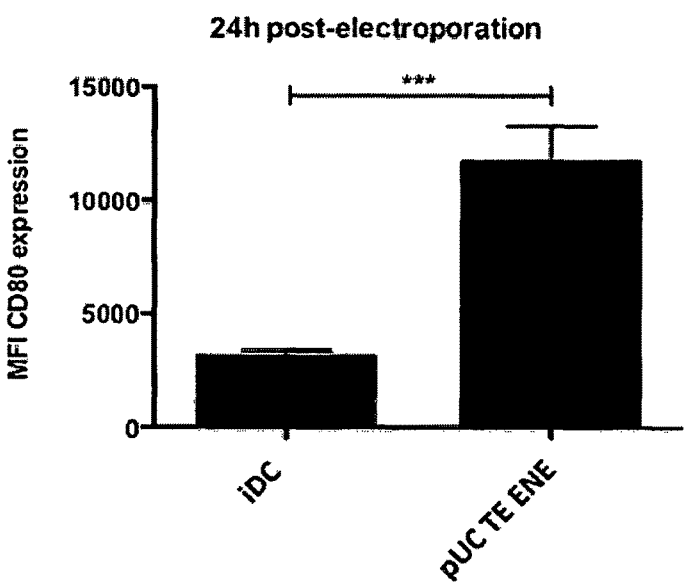

FIG. 4C: Phenotype of immature and mature DCs. MFI values of the indicated molecules were investigated 24h post-electroporation of iDCs. Data are represented as mean ±SEM. (Paired t test, *P<0.05; P<0.01; *P<0.001). CD40 N=9; CD70 N=19; CD80 N=12; CD 83 N=12; CCR7 N=12.

Figure 4D:
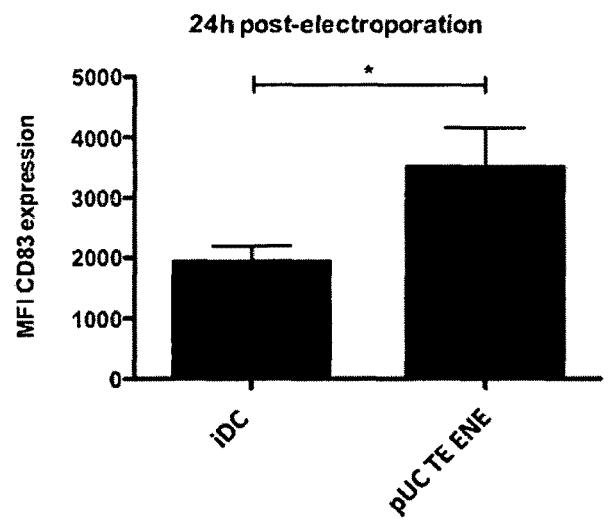

FIG. 4D: Phenotype of immature and mature DCs. MFI values of the indicated molecules were investigated 24h post-electroporation of iDCs. Data are represented as mean ±SEM. (Paired t test, *P<0.05; P<0.01; *P<0.001). CD40 N=9; CD70 N=19; CD80 N=12; CD 83 N=12; CCR7 N=12.

Figure 4E:
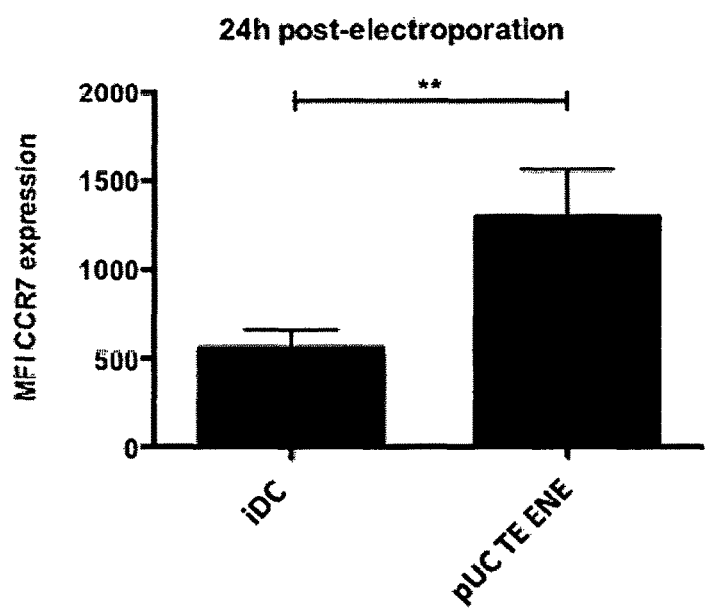

FIG. 4E: Phenotype of immature and mature DCs. MFI values of the indicated molecules were investigated 24h post-electroporation of iDCs. Data are represented as mean ±SEM. (Paired t test, *P<0.05; P<0.01; *P<0.001). CD40 N=9; CD70 N=19; CD80 N=12; CD 83 N=12; CCR7 N=12.

Figure 5A:
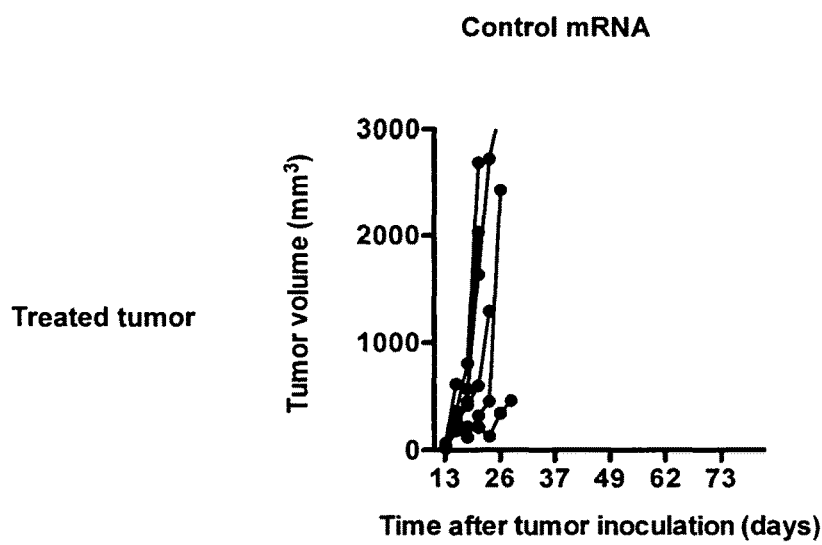

FIG. 5A: Two-side tumor model with P815: single treatment of one tumor with tNGFR as a control or with pUC TE ENE TriMix. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 5B:
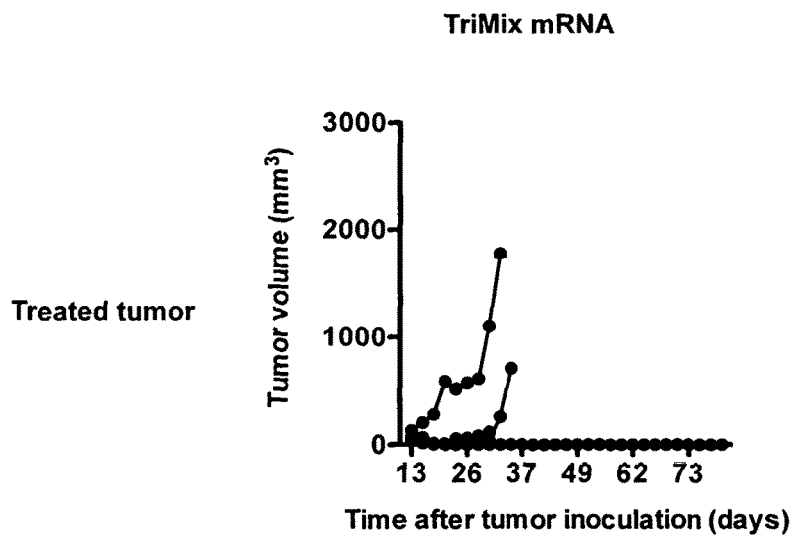

FIG. 5B: Two-side tumor model with P815: single treatment of one tumor with tNGFR as a control or with pUC TE ENE TriMix. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 5C:
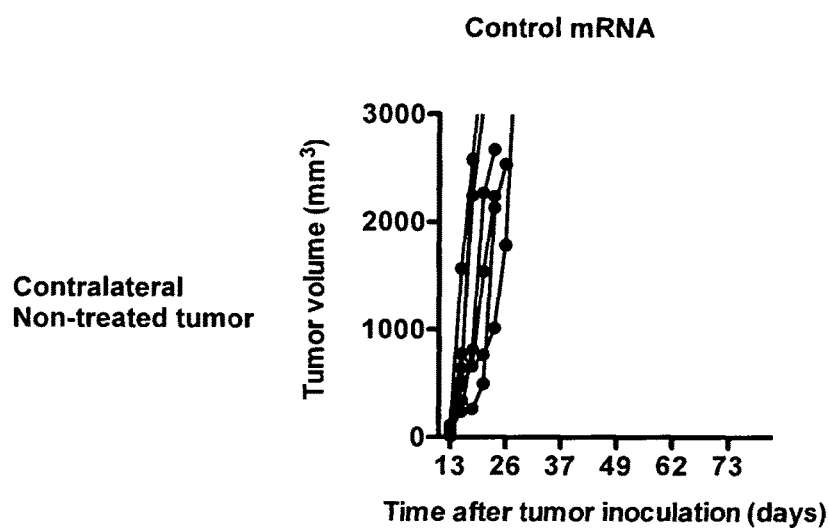

FIG. 5C: Two-side tumor model with P815: single treatment of one tumor with tNGFR as a control or with pUC TE ENE TriMix. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 5D:
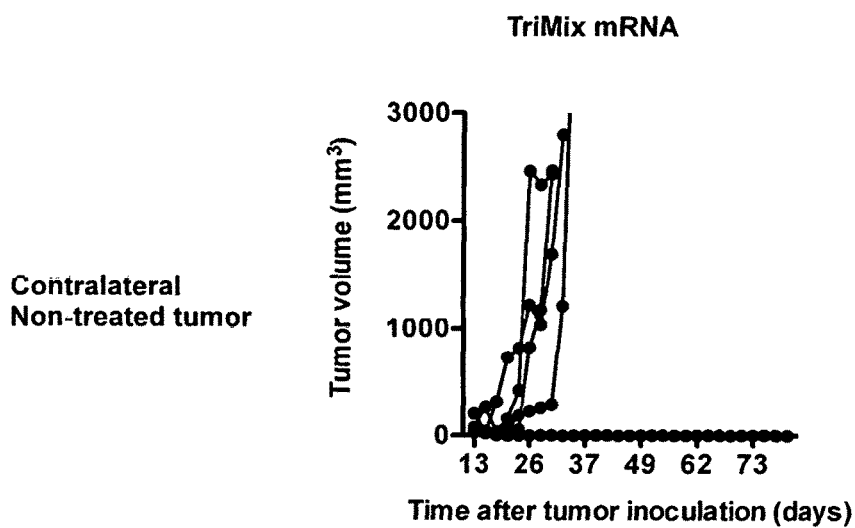

FIG. 5D: Two-side tumor model with P815: single treatment of one tumor with tNGFR as a control or with pUC TE ENE TriMix. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 5E:
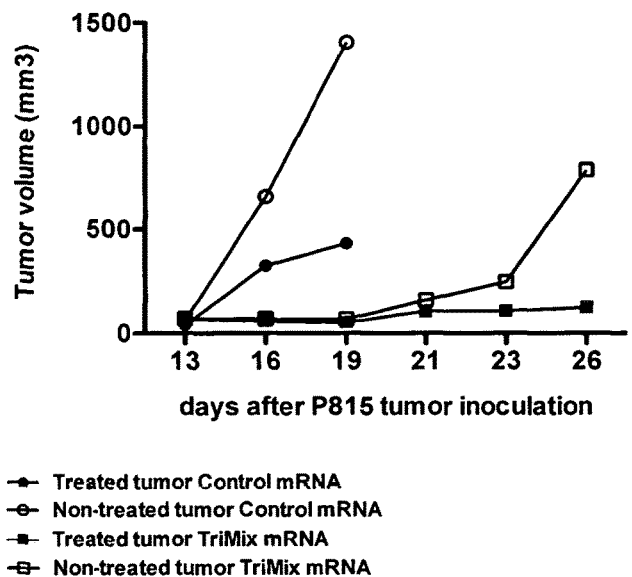

FIG. 5E: Two-side tumor model with P815: single treatment of one tumor with tNGFR as a control or with pUC TE ENE TriMix. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 5F:
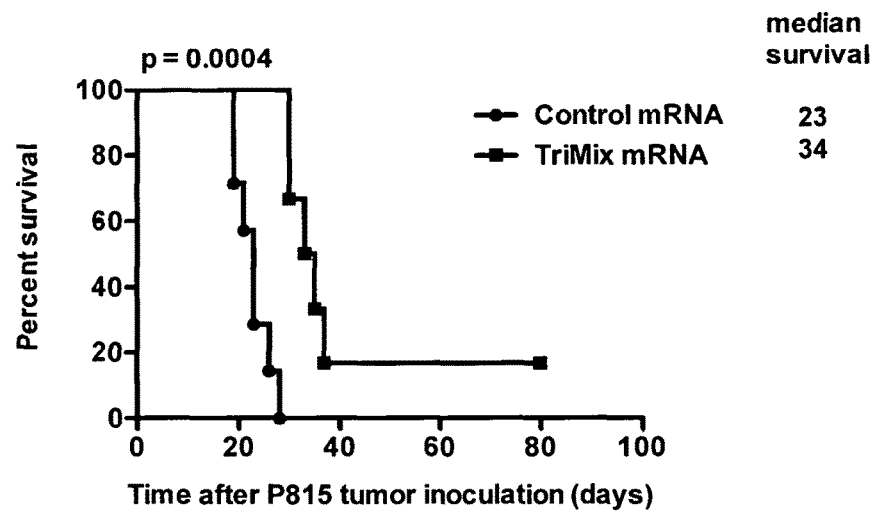

FIG. 5F: Two-side tumor model with P815: single treatment of one tumor with tNGFR as a control or with pUC TE ENE TriMix. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 6A:
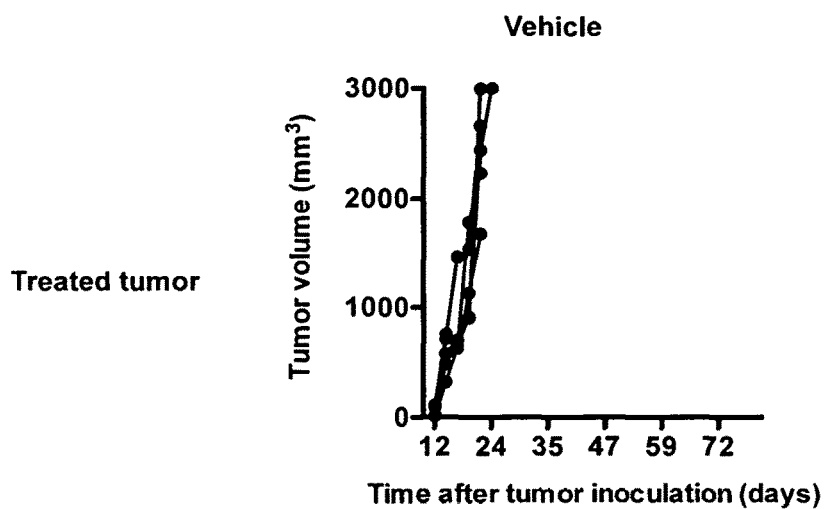

FIG. 6A: Two-side tumor model with P815: single treatment of one tumor, with tNGFR or 0.8 volumes of Hartman solution served as a control. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 6B:
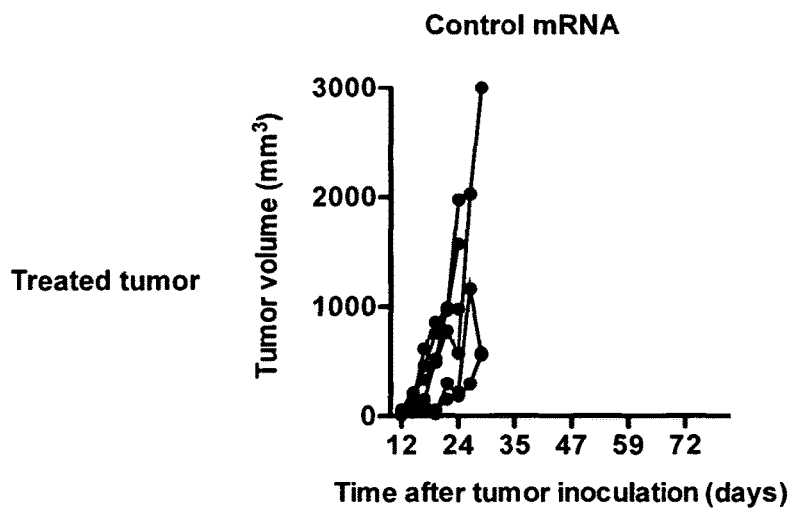

FIG. 6B: Two-side tumor model with P815: single treatment of one tumor, with tNGFR or 0.8 volumes of Hartman solution served as a control. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 6C:
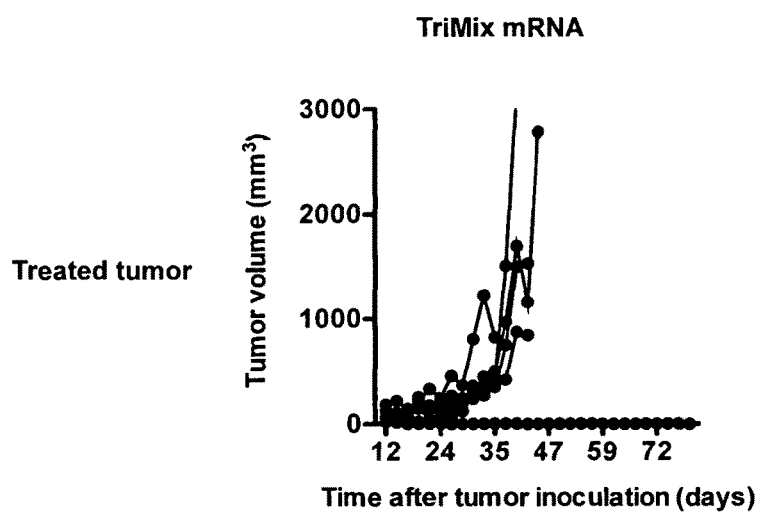

FIG. 6C: Two-side tumor model with P815: single treatment of one tumor, with tNGFR or 0.8 volumes of Hartman solution served as a control. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 6D:
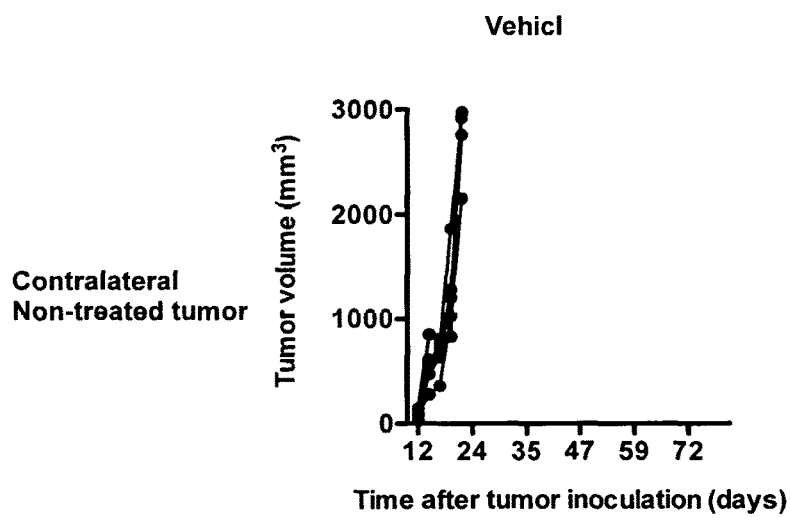

FIG. 6D: Two-side tumor model with P815: single treatment of one tumor, with tNGFR or 0.8 volumes of Hartman solution served as a control. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 6E:
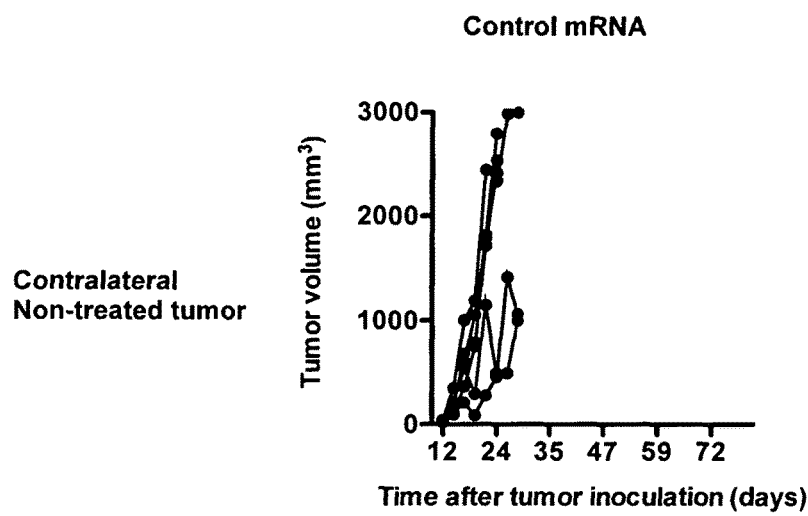

FIG. 6E: Two-side tumor model with P815: single treatment of one tumor, with tNGFR or 0.8 volumes of Hartman solution served as a control. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 6F:
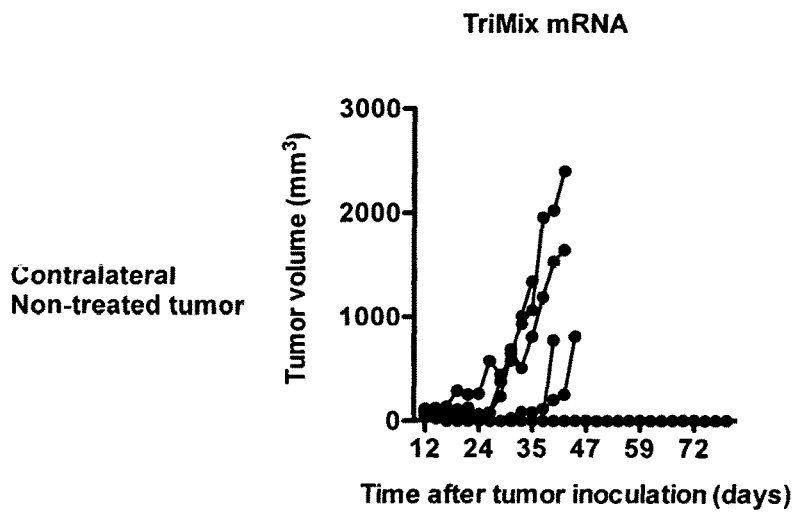

FIG. 6F: Two-side tumor model with P815: single treatment of one tumor, with tNGFR or 0.8 volumes of Hartman solution served as a control. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 6G:
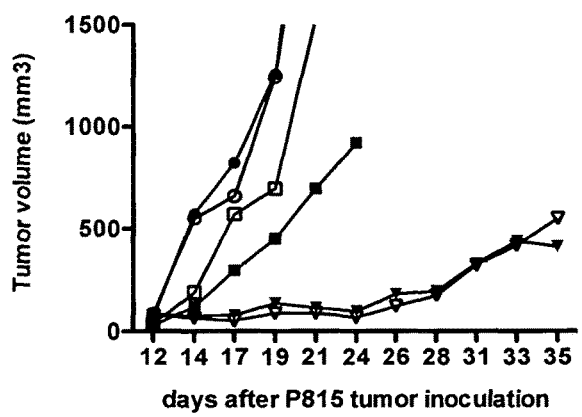

FIG. 6G: Two-side tumor model with P815: single treatment of one tumor, with tNGFR or 0.8 volumes of Hartman solution served as a control. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

Figure 6H:
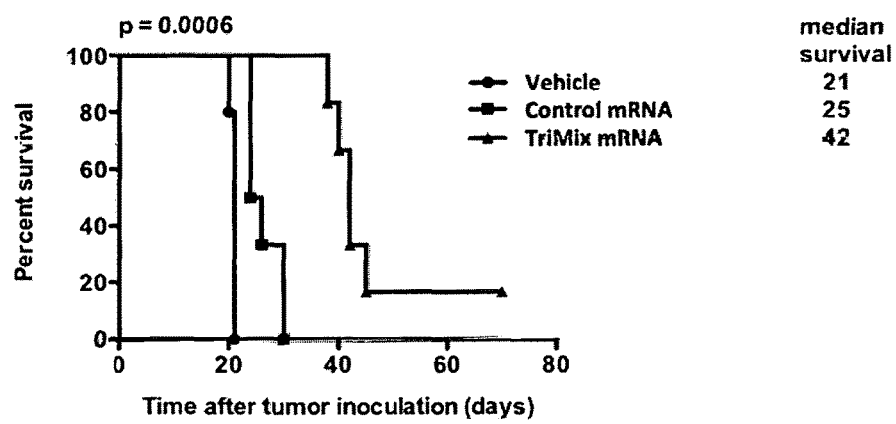

FIG. 6H: Two-side tumor model with P815: single treatment of one tumor, with tNGFR or 0.8 volumes of Hartman solution served as a control. The contralateral, non-treated tumor was used to evaluate the systemic anti-tumor immune response. Tumor growth was shown for each individual mouse per group (n=6) followed by an overview of the mean tumor volume. Survival was visualized in a Kaplan-Meier plot. Differences in survival were analyzed by the log-rank test.

FIG. 7: The pUC TE ENE-vector with its most important elements.

FIG. 8: Shows a sequence comparison of 3 variable TE sequences (SEQ ID No 1, 2 and 3) as created by Clustal 2.1 from EMBL.

Figure 9A:
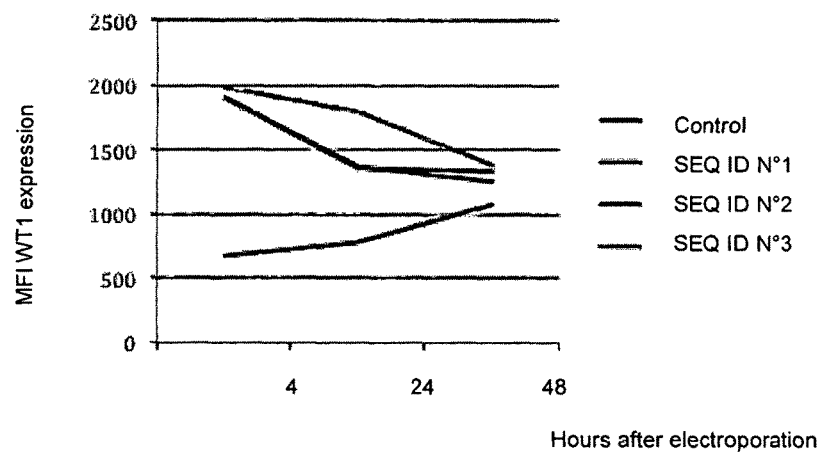

FIG. 9A: WT1 expression in DCs electroporated with WT1 mRNA. iDCs were electroporated with 10 μg WT1 mRNA encoded by the different vectors and analyzed for their WT1 expression by intracellular staining 4 h, 24 h, and 48 h post-electroporation. A comparison of MFI values after electroporation of the iDCs with the different WT1-encoding vectors is shown. N=3

Figure 9B:
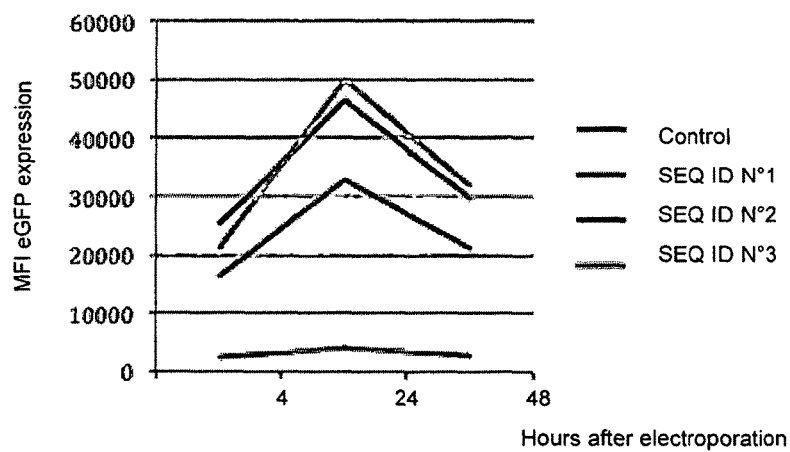

FIG. 9B: eGFP expression in DCs electroporated with eGFP mRNA. iDCs were electroporated with 10 μg eGFP mRNA encoded by the different vectors and analyzed for their eGFP expression by intracellular staining 4 h, 24 h, and 48 h post-electroporation. A comparison of MFI values after electroporation of the iDCs with the different WT1-encoding vectors is shown. N=3

DETAILED DESCRIPTION OF THE INVENTION

In a first aspect the present invention provides a nucleic acid vector comprising a translation enhancer (TE) and a nuclear retention sequence. More in particular, said nucleic acid vector comprises a translation enhancer (TE) sequence having at least 80% sequence identity to SEQ ID No1, a transcribable nucleic acid sequence and a nuclear retention sequence represented by SEQ ID No4.

The term "vector" is used here in its most general meaning and comprises any intermediate vehicles for a nucleic acid, which, for example, enable said nucleic acid to be introduced into prokaryotic and/or eukaryotic host cells and, where appropriate, to be integrated into a genome. Such vectors are preferably replicated and/or expressed in the cell. Vectors comprise plasmids, phagemids or virus genomes. The term "plasmid", as used herein, generally relates to a construct of extrachromosomal genetic material, usually a circular DNA duplex, which can replicate independently of chromosomal DNA.

According to the invention, a nucleic acid molecule or a nucleic acid sequence refers to a nucleic acid which is preferably deoxyribonucleic acid (DNA) or ribonucleic acid (RNA). According to the invention, nucleic acids comprise genomic DNA, cDNA, mRNA, recombinantly prepared and chemically synthesized molecules. According to the invention, a nucleic acid may be in the form of a single-stranded or double stranded and linear or covalently closed circular molecule. The term "nucleic acid" furthermore also comprises a chemical derivatization of a nucleic acid on a nucleotide base, on the sugar or on the phosphate, and nucleic acids containing non-natural nucleotides and nucleotide analogs.

The nucleic acids described according to the invention are preferably isolated. The term "isolated nucleic acid" means according to the invention that the nucleic acid has been 1/ amplified in vitro, for example by polymerase chain reaction (PCR) 2/ recombinantly produced by cloning; 3/ purified, for example by cleavage and gel-electrophoretic fractionation, or 4/ synthesized, for example by chemical synthesis. An isolated nucleic acid is a nucleic acid available to manipulation by recombinant DNA techniques.

5' Translation Enhancer (TE)

Posttranscriptional regulation of translation is mainly controlled at the translation initiation phase. A complex of initiation factors binds to the 5'CAP structure and recruits the ribosomal subunits. This complex then starts a scanning movement along the mRNA until an AUG codon in a suitable context is encountered. The efficiency of this process can be controlled by numerous structural features in both 5' and 3' UTRs (UnTranslated Regions) of the mRNA. These features include TOP (Terminal OligoPyrimidine tract) regions, IRES (Internal Ribosome Entry Site) and Upstream ORF's (Open Reading Frames) in the 5' UTR. In the 3' UTR CITE (Cap Independent Translation Enhancer) motifs have been described. The length of the poly-A tail has also been shown to play an important role in translation initiation, since PABP (Poly-A Binding Protein) needs to associate to both the poly-A tail and the eIF4 complex on the CAP site.

IRES is a motif that is able to recruit ribosomes independently of interaction with the 5'CAP structure. The first IRES elements were described in picornaviruses (e.g. EMCV, EncephaloMyoCarditisVirus). During infection CAP dependent translation is shut down, yielding an advantage to the CAP independent translation of the viral proteins. Several eukaryotic IRES sequences have been described in recent years. In stress situations CAP dependent translation is down regulated, while CAP independent translation of some essential genes can continue. More specifically, dendritic cells that are activated by e.g. ligation of LPS on Toll Like Receptor 4 also shut down CAP dependent translation, while CAP independent translation of some genes protects the cells from apoptosis.

Hu et al. studied a sequence in the 5' leader of the mRNA coding for the mouse Gtx homeodomain protein. They described a sequence that is complementary to sequences in the 18S ribosomal RNA. They found that this motif had a profound influence on the efficiency of translation (Hu et al., 1999).

Later, it was shown that this motif functions as an internal ribosome entry site (IRES) and showed that shorter non-overlapping segments of this 5'leader could enhance the translation of a second cistron in a dicistronic mRNA. One of these segments was 9 nucleotides in length and when multiple copies of this IRES module were linked together, IRES activity was greatly enhanced. A tandem repeat of the same 9n segment, interspaced by 9n fragments of the human beta globin 5' UTR, was shown to function as a Translation Enhancer (TE) in a monocistronic mRNA when positioned at the 5'-end of mRNA, in front of the ORF.

Hence, in the context of the present invention, any sequence functioning as a Translation Enhancer for mRNA may be used, for example those elements described herein above. In particular, a translation enhancer is a sequence in the transcribed RNA that facilitates translation. One possible mode of action is through enhancing the binding of the ribosome to the 5' end of the mRNA.

In a particular example, the vector according to this invention may yield RNA that contains a 10× tandem repeat of the wild type 9n sequence from the Gtx leader sequence: CCGGCGGGT. These motifs are linked by a 9n sequence derived from the 5' UTR of human beta globin: TTCTGACAT. This DNA fragment can be cloned in the plasmid between the bacteriophage promotor sequence and the ORF (Open Reading Frame).

In a particular embodiment, the translation enhancer according to the present invention has at least 80% sequence identity to SEQ ID No1. As evident from FIG. 8, SEQ ID No 2 and 3 have a sequence identity of at least 80% in comparison to SEQ ID No1, and are thus suitable to used in connection with the present invention. More preferably, the translation enhancer according to the present invention has at least 85%, 86%, 87%, 88% or 89% sequence identity to SEQ ID No1. As evident from FIG. 8, SEQ ID No 2 and 3 have a sequence identity of at least 85% in comparison to SEQ ID No1. Even more preferably, the translation enhancer according to the present invention has at least 90%, 91%, 92%, 93%, 94%, 95%, 96%, 97%, 98% 99% or 100% sequence identity to SEQ ID No1. As evident from FIG. 8, SEQ ID No 3 has a sequence identity of at least 90% in comparison to SEQ ID No1. Even more preferably, the translation enhancer is represented by anyone of SEQ ID No1, 2 or 3; most preferably SEQ ID No1.

Nuclear Retention Sequence

The importance of post-transcriptional genetic control processes has become increasingly apparent in recent years. Among these processes, one that began to receive considerable attention is the control of mRNA stability. With the growing recognition that mRNA degradation has a profound impact on gene expression and that rates of mRNA decay can be modulated in response to environmental and developmental signals, a vigorous research effort aimed at understanding this process is now taking place. Significant progress has been made and studies over the past 20 years have elucidated a number of general features of mRNA degradation.

Both cellular and viral mRNAs are subject to robust RNA decay pathways. Viruses have developed different methods to protect their mRNA from deadenylation mechanisms of the host. The poly-adenylated non-translated RNA (PAN) of Kaposi's sarcoma associated Herpes virus (KSHV) is very abundant in the nucleus of infected cells. This RNA is resistant to deadenylation and degradation. The accumulation of PAN depends on the activity of a 79 nucleotide RNA element in the 3' region, called the ENE (Expression and Nuclear retention Element). Conrad et al. published in 2005 the first article related to ENE in describing it as a Kaposi's sarcoma virus RNA element that gave an increased nuclear abundance of intronless transcripts (Conrad, 2005). The ENE fragment contains a specific U-rich hairpin structure that interacts with the poly-A tail. As such, a secondary structure is obtained which results in the retention of the RNA in the nucleus and hence the name Nuclear Retention Element. A secondary effect, is the interaction of the U-rich hairpin structure with the poly-A tail of mRNA resulting in a 'shielding' effect from degradation by the host, a trait that is of particular interest in the production of mRNA for immunotherapeutic purposes.

Polyadenylated nuclear (PAN) RNA (also known as T1.1 or nut-1 RNA) is a lncRNA produced by the oncogenic gammaherpesvirus, Kaposi's sarcoma-associated herpesvirus (KSHV) (Sun et al., 1996). PAN RNA accumulates to extraordinarily high levels (~500,000 copies/cell) during lytic infection and is required for the production of late viral proteins and infectious virus (Sun et al., 1996). The expression and nuclear retention element (ENE), located ~120 nts upstream of PAN RNA's polyadenylation site, is essential for this high accumulation in the nucleus (Conrad and Steitz, 2005). The ENE inhibits rapid decay of PAN RNA by blocking deadenylation (Conrad et al., 2006). PAN RNA does not yield protein expression. The nuclear retention keeps the RNA away from the translation machinery in the cytoplasm, while the shielding of the poly-A tail prohibits binding to the PABP (polyA binding protein) which is essential for efficient translation. Hence, use of this sequence in transfection is not obvious.

The KSHV ENE is a 79 nt-long RNA element, composed of a stem-loop structure with an asymmetric internal U-rich loop, which in conjunction with adjacent base pairs constitutes the ENE's functional core. The crystal structure of the ENE core bound to oligo(A)9 revealed 5 consecutive U-A-U base triples formed between the U-rich loop and oligo(A)9 (Mitton-Fry et al., 2010), which are extended by A-minor interactions with three G-C base pairs of the lower stem. Genetic and biochemical analyzes indicate similar interactions between the PAN RNA's poly(A) tail and the ENE in vivo (Mitton-Fry et al., 2010).

Hence, in the context of the present invention, any sequence functioning as a nuclear retention element for mRNA may be used, for example those elements described herein above. In particular, a nuclear retention element is a cis acting sequence that has the capacity to protect the mRNA to cytoplasmic decay.

In a particular embodiment, the nuclear retention element also functions as an RNA stabilizing sequence.

In a particular example, the nuclear retention element is the Expression and Nuclear retention Element of KSHV. A 79 bp sequence isolated from the PAN (Poly Adenylated Non translated) RNA is placed upstream from the A124 stretch in the RNA production plasmid. The ENE forms a U rich loop that associates with the polyA tail and protects it from degradation.

In a particular embodiment, the nuclear retention element according to the present invention is represented by SEQ ID No4.

Further Elements in the Vector of the Present Invention

In a further embodiment, the nucleic acid vector of the present invention, may contain further elements selected from the list comprising a bacteriophage promoter, a transcribable nucleic acid sequence and a poly-A tail.

Messenger RNA or ribonucleic acid (mRNA) consists of a single-stranded polymer of 4 nucleotides (adenosine, guanosine, cytidine and uridine monophosphate). A 5'-end modification or 5'CAP is needed for recognition of the mRNA by the translation initiation complex, proper attachment of the mRNA to the ribosomes, as well as protection from 5' exonucleases. This modification consists of a 7-methylguanosine nucleotide added to the first transcribed nucleotide. The coding region begins with a start codon (usually AUG) and ends with a stop codon (usually UAA, UAG or UGA). Before the start codon and after the stop codon, mature mRNA contains a 5' untranslated region (UTR) and a 3' UTR. These regions contribute to the mRNA stability or instability and translational efficiency.

A transcribable nucleic acid sequence, in particular a nucleic acid coding for a peptide or protein, and an expression control sequence are "functionally" linked to one another, if they are covalently linked to one another in such a way that transcription or expression of the transcribable and in particular coding nucleic acid is under the control or under the influence of the expression control sequence.

The nucleic acids specified herein, in particular transcribable and coding nucleic acids, may be combined with any expression control sequence, in particular promoters, which may be homologous or heterologous to said nucleic acids, with the term "homologous" referring to the fact that a nucleic acid is also functionally linked naturally to the expression control sequence, and the term "heterologous" referring to the fact that a nucleic acid is not naturally functionally linked to the expression control sequence.

The term "expression control sequences" comprises according to the invention promoters, ribosome-binding sequences and other control elements, which control transcription of a gene or translation of the derived RNA. In particular embodiments of the invention, the expression control sequences can be regulated. The precise structure of expression control sequences may vary depending on the species or cell type but usually includes 5'-untranscribed and 5'- and 3-untranslated sequences involved in initiating transcription and translation, respectively, such as a TATA box, capping sequence, CAAT sequence and the like. More specifically, 5'-untranscribed expression control sequences include a promoter region which encompasses a promoter sequence for transcription control of the functionally linked gene. Expression control sequences may also include enhancer sequences or upstream activator sequences.

In particular embodiments, a nucleic acid is functionally linked according to the invention to expression control sequences, which may be homologous or heterologous with respect to the nucleic acid.

The term "promoter" or "promoter region" refers to a DNA sequence upstream (5') of the coding sequence of a gene, which controls expression of said coding sequence by providing a recognition and binding site for RNA polymerase. The promoter region may include further recognition or binding sites for further factors involved in regulating transcription of said gene. A promoter may control transcription of a prokaryotic or eukaryotic gene. A promoter may be "inducible" and initiate transcription in response to an inducer, or may be "constitutive" if transcription is not controlled by an inducer. An inducible promoter is expressed only to a very small extent or not at all, if an inducer is absent. In the presence of the inducer, the gene is "switched on" or the level of transcription is increased. This is usually mediated by binding of a specific transcription factor.

In a particular embodiment, the transcribable nucleic acid sequence is selected from the list comprising mRNA encoding CD40L (NM_000074), CD70 (NM_001252), caTLR4 ((a truncated version of the human TLR4 gene, that contains only the transmembrane and cytoplasmic region of the gene, preceded by the signal peptide of LAMP1 (lysosome associated membrane protein)) or antigen/disease specific mRNA.

The bacteriophage promotor according to this invention, may be any suitable promotor for RNA transcription and is preferably selected from the list comprising T7 promotor, SP6 promotor and T3 promotor; more in particular T7 promotor.

The poly-A tail as used in the context of this invention, preferably consists of between and about 100-150 adenosines, more in particular 120-125 adenosines, preferably about 124 adenosines.

The terms "polyadenyl cassette" or "poly-A sequence" refer to a sequence of adenyl residues which is typically located at the 3' end of an RNA molecule. The invention provides for such a sequence to be attached during RNA transcription by way of a DNA template on the basis of repeated thymidyl residues in the strand complementary to the coding strand, whereas said sequence is normally not encoded in the DNA but is attached to the free 3' end of the RNA by a template-independent RNA polymerase after transcription in the nucleus. According to the invention, a poly(A) sequence of this kind is understood as meaning a nucleotide sequence of at least 20, preferably at least 40, preferably at least 80, preferably at least 100 and preferably up to 500, preferably up to 400, preferably up to 300, preferably up to 200, and in particular up to 150 consecutive A nucleotides, and in particular about 120 consecutive A nucleotides, wherein the term "A nucleotides" refers to adenyl residues.

The invention further provides an RNA molecule obtainable by transcription of the nucleic acid vector according to this invention.

In a further aspect, the present invention provides a method of increasing stability and/or translation efficiency of in vitro transcribed RNA; said method comprising the steps of:
  (i) providing a vector according to this invention wherein said transcribable nucleic acid sequence is a transcribable DNA sequence, which corresponds to said RNA to be transcribed; and
  (ii) transcribing in vitro the transcribable DNA sequence; as well as an RNA molecule obtainable by said method.

According to the invention, the term "transcription" comprises "in vitro transcription" wherein the term "in vitro transcription" relates to a method in which RNA, in particular mRNA, is synthesized in vitro in a cell-free manner. The preparation of transcripts preferably makes use of cloning vectors which are generally referred to as transcription vectors and which are included according to the invention under the term "vector".

The term "nucleic acid sequence transcribed from a nucleic acid sequence" refers to RNA, where appropriate as a part of a complete RNA molecule, which is a transcription product of the latter nucleic acid sequence.

The term "nucleic acids which can be transcribed to give a common transcript" means that said nucleic acids are functionally linked to one another in such a way that, where appropriate after linearization such as restriction enzyme cleavage of the nucleic acid molecule comprising said nucleic acids, in particular of a closed circular nucleic acid molecule, transcription under the control of a promoter results in an RNA molecule comprising the transcripts of said nucleic acids covalently bound to one another, where appropriate separated by sequences located in-between.

According to the invention, the term "expression" is used in its most general meaning and comprises production of RNA and/or protein. It also comprises partial expression of nucleic acids. Furthermore, expression may be transient or stable. With respect to RNA, the term "expression" or "translation" refers in particular to production of peptides or proteins.

The term "nucleic acid sequence which is active in order to increase the translation efficiency and/or stability of a nucleic acid sequence" means that the first nucleic acid is capable of modifying, in a common transcript with the second nucleic acid, the translation efficiency and/or stability of said second nucleic acid in such a way that said translation efficiency and/or stability is increased in comparison with the translation efficiency and/or stability of the said second nucleic acid without said first nucleic acid. In this context, the term "translation efficiency" relates to the amount of translation product provided by an RNA molecule within a particular period of time and the term "stability" relates to the half-life of an RNA molecule.

In a particular embodiment, the present invention provides an RNA molecule comprising a translation enhancer (TE) and a nuclear retention element (ENE); or a composition comprising one or more of said RNA molecules. More in particular, the present invention provides an RNA molecule comprising a translation enhancer (TE) having at least 80% sequence identity to SEQ ID No1, a transcribable nucleic acid sequence, and a nuclear retention sequence represented by SEQ ID No4; or a composition comprising said RNA molecule.

Said RNA molecule may further comprise one or more elements selected from the list comprising a translatable nucleic acid sequence, and a poly-A tail; wherein said translatable nucleic acid sequence may be selected from the list comprising mRNA encoding CD40L, CD70, caTLR4 or antigen/disease specific mRNA.

In the context of the present invention, the TE element is preferably positioned at the 5' end of the transcribable/translatable RNA molecule and the nuclear retention sequence (ENE) preferably at the 3' end.

"3' end of a nucleic acid" refers according to the invention to that end which has a free hydroxyl group. "5' end of a nucleic acid" refers according to the invention to that end which has a free phosphate group.

In the context of the present invention "mRNA" means "messenger RNA" and refers to a transcript which is produced using DNA as template and which itself codes for a peptide or protein. An mRNA typically comprises a 5'-untranslated region, a protein-encoding region and a 3'-untranslated region. mRNA has a limited half time in cells. According to the invention, mRNA may be prepared from a DNA template by in vitro transcription. It may be modified by further stabilizing modifications and capping, in addition to the modifications according to the invention.

In a particular embodiment, the composition according to this invention comprises mRNA encoding CD40L, CD70 and caTLR4 either or not in combination with mRNA encoding antigen/disease specific mRNA.

The antigen/disease specific mRNA according to the present invention may be selected from the non-limiting list comprising tumor antigens, pathogen derived antigens, allergens . . .

The present invention further provides the use of the RNA molecule(s) and/or composition(s) comprising one or more of said RNA molecules for multiple purposes, such as for example for in vivo or in vitro introduction in a host cell; or for use in medicine.

It is also an aspect of the present invention to provide a kit comprising one or more vectors; one or more RNA molecules or a composition according to the present invention.

The present invention also provides a method for treating a patient in need thereof with one or more RNA molecules or a composition according to the invention; wherein, said RNA molecules can be administered simultaneously or sequentially with intervals.

The invention provides for nucleic acids in particular RNA to be administered to a patient. Nucleic acids can be administered by ex vivo methods, i.e. by removing cells from a patient, genetically modifying said cells (e.g. by transfection) and reintroducing the modified cells into the patient. Transfection and transduction methods are known to the skilled worker. The invention also provides for nucleic acids to be administered in vivo.

According to the invention, the term "transfection" refers to introducing one or more nucleic acids into an organism or into a host cell. Various methods may be employed in order to introduce according to the invention nucleic acids into cells in vitro or in vivo. Such methods include transfection of nucleic acid-CaP04 precipitates, transfection of nucleic acids associated with DEAE, transfection of infection with viruses carrying the nucleic acids of interest, liposome mediated transfection, and the like. In particular embodiments, preference is given to directing the nucleic acid to particular cells. In such embodiments, a carrier used for administering a nucleic acid to a cell (e.g. a retrovirus or a liposome) may have a bound targeting molecule. For example, a molecule such as an antibody specific to a surface membrane protein on the targeted cell, or a ligand for a receptor on the target cell may be incorporated into or bound to the nucleic acid carrier. If administration of a nucleic acid by liposomes is desired, proteins binding to a surface membrane associated with endocytosis may be incorporated into the liposome formulation in order to enable targeting and/or absorption. Such proteins include capsid proteins or fragments thereof which are specific to a particular cell type, antibodies to proteins that are internalized, proteins targeting an intracellular site, and the like.

The RNA molecules or compositions according to the present invention may be administered to a patient in need thereof by any suitable administration route such as for example intranodal, intradermal, intralymphatic and intratumoral. Furthermore, when treating for example cancer patients, the administration of the RNA molecules or compositions according to this invention, may be used in combination with methods for releasing tumor mRNA from the tumor in the patient, such as for example ablation or sonoporation.

According to the invention, standard methods may be used for preparing recombinant nucleic acids, culturing cells, in particular electroporation and lipofection. Enzymatic reactions are carried out according to the manufacturer's instructions or in a manner known per se.

According to the invention, a "nucleic acid sequence which is derived from a nucleic acid sequence" refers to a nucleic acid containing, in comparison with the nucleic acid from which it is derived, single or multiple nucleotide substitutions, deletions and/or additions and which is preferably complementary to the nucleic acid from which it is derived, i.e. there is a certain degree of homology between said nucleic acids and the nucleotide sequences of said nucleic acids correspond in a significant direct or complementary manner.

According to the invention, a nucleic acid derived from a nucleic acid has a functional property of the nucleic acid from which it is derived. Such functional properties include in particular the ability to increase, in a functional linkage to a nucleic acid which can be transcribed into RNA (transcribable nucleic acid sequence), the stability and/or translation efficiency of RNA produced from this nucleic acid in the complete RNA molecule.

A nucleic acid is "complementary" to another nucleic acid if the two sequences can hybridize with one another and form a stable duplex, said hybridization being carried out preferably under conditions which allow specific hybridization between polynucleotides (stringent conditions). Stringent conditions are described, for example in Molecular Cloning: A laboratory manual, J Sambrook et al.

According to the invention, complementary nucleic acids have nucleotides, which are at least 60%, at least 70%, at least 80%, at least 90%, and preferably at least 95%, at least 98% or at least 99% identical.

According to the invention, a first polynucleotide region is considered to be located downstream of a second polynucleotide region, if the 5' end of said first polynucleotide region is the part of said first polynucleotide region closest to the 3' end of said second polynucleotide region.

The 3'-untranslated region typically extends from the termination codon for a translation product to the poly-A sequence which is usually attached after the transcription process. The 3'-untranslated regions of mammalian mRNA typically have a homology region known as the AAUAAA hexanucleotide sequence. This sequence is presumably the poly-A attachment signal and is frequently located from 10 to 30 bases upstream of the poly-A attachment site.

3'-untranslated regions may contain one or more inverted repeats which can fold to give stem-loop structures, which act as barriers for exoribonucleases or interact with proteins known to increase RNA stability (e.g. RNA-binding proteins).

5'- and/or 3'-untranslated regions may, according to the invention, be functionally linked to a transcribable and in particular coding nucleic acid, so as for these regions to be associated with the nucleic acid in such way that the stability and/or translation efficiency of the RNA that is transcribed from said transcribable nucleic acid are increased.

According to the invention, the term "gene" refers to a particular nucleic acid sequence, which is responsible for producing one or more cellular products and/or for achieving one or more cellular products and/or for achieving one or more intercellular or intracellular functions. More specifically, said term relates to a DNA section, which comprises a nucleic acid coding for a specific protein or a functional or structural RNA molecule.

According to the invention, the term "host cell" refers to any cell which can be transformed or transfected with an exogenous nucleic acid. The term "host cell" comprises, according to the invention prokaryotic (e.g. *E. coli*) or eukaryotic cells (e.g. yeast cells and insect cells). Particular preference is given to mammalian cells such as cells from humans, mice, hamsters, pigs, goats, and primates. The cells may be derived from a multiplicity of tissue types and comprise primary cells and cell lines. Specific examples include keratinocytes, peripheral blood leukocytes, bone marrow stem cells and embryonic stem cells. In other embodiments, the host cell is an antigen-presenting cell, in particular a dendritic cell, a monocyte or a macrophage. A nucleic acid may be present in the host cell in a single or in several copies and, in one embodiment is expressed in the host cell.

According to the invention, a peptide or protein encoded by a nucleic acid may be a peptide or protein which is located in the cytoplasm, in the nucleus, in the membrane, in organelles or in secreted form. They include structural proteins, regulatory proteins, hormones, neurotransmitters, growth-regulating factors, differentiation factors, gene expression regulating factors, DNA-associated proteins, enzymes, serum proteins, receptors, medicaments, immunomodulators, oncogenes, toxins, tumor antigens or antigens. Said peptides or proteins may have a naturally occurring sequence or a mutated sequence in order to enhance, inhibit, regulate or eliminate their biological activity.

The term "peptide" refers to substances which comprise two or more, preferably 3 or more, preferably 4 or more, preferably 6 or more, preferably 8 or more, preferably 10 or more, preferably 13 or more, preferably 16 or more, preferably 100 or preferably 150 consecutive amino acids linked to one another via peptide bonds. The term "protein" refers to large peptides, preferably peptides having at least 151 amino acids, but the terms "peptide" and "protein" are used herein usually as synonyms. The terms "peptide" and "protein" comprise according to the invention substances which contain not only amino acid components but also non-amino acid components such as sugars and phosphate structures, and also comprise substances containing bonds such as ester, thioether or disulphide bonds.

"Reporter" relates to a molecule, typically a peptide or protein, which is encoded by a reporter gene and measured in a reporter assay. Conventional systems usually employ an enzymatic reporter and measure the activity of said reporter.

According to the invention, two elements, such as nucleotides or amino acids are consecutive, if they are directly adjacent to one another, without any interruption.

"Restriction endonucleases" or "restriction enzymes" refer to a class of enzymes that cleave phosphodiester bonds in both strands of a DNA molecule within specific base sequences. They recognize specific binding sites, referred to as recognition sequences, on a double stranded DNA molecule. The sites at which said phosphodiester bonds in the DNA are cleaved by said enzymes are referred to as cleavage sites. In the case of type IIS enzymes, the cleavage site is located at a defined distance form the DNA binding site.

Areas Of Application

An area of application of the present invention is vaccination, i.e. the use of modified mRNA for inoculation or the use of a pharmaceutical composition comprising the modified mRNA as an inoculating agent, or the use of modified mRNA in the preparation of a pharmaceutical composition for inoculation purposes. Vaccination is based on introducing an antigen into an organism or subject, in particular into a cell of the organism or subject. In the context of the present invention, the genetic information encoding the antigen is introduced into the organism or subject in the form of a modified mRNA encoding the antigen and/or the different TriMix mRNA strands. The modified 'antigen' mRNA contained in the pharmaceutical composition is translated into an antigen, i.e. the polypeptide or antigenic peptide coded by the modified mRNA is expressed and an immune response directed against the polypeptide or antigenic peptide is stimulated. For vaccination against a pathogenic organism, e.g, a virus, a bacterium, or a protozoan, a surface antigen of such an organism may be used as an antigen against which an immune response is elicited. In the context of the present invention, a pharmaceutical composition comprising the modified mRNA encoding such a surface antigen may be used as a vaccine. In applications wherein a genetic vaccine is used for treating cancer, the immune response is directed against tumour antigens by generating a modified mRNA encoding a tumour antigen(s), in particular a protein which is expressed exclusively on cancer cells. Such a modified mRNA encoding a tumour antigen may be used alone or as a component of a pharmaceutical composition according to the invention, wherein administration of either the modified mRNA or a composition thereof results in expression of the cancer antigen(s) in the organism. An immune response to such a vaccine would, therefore, confer to the vaccinate subject a degree of protective immunity against cancers associated with the immunizing cancer antigen. Alternatively, such measures could be used to vaccinate a cancer patient with a modified mRNA encoding a tumour antigen(s) expressed on the patient's cancer cells so as to stimulate the cancer patient's immune response to attack any cancer cells expressing the encoded antigen.

For gene therapy applications, for example wherein a pharmaceutical composition of the invention is used, the modified mRNA therein codes for at least one biological active peptide or polypeptide that is not formed or is only insufficiently or defectively formed in the patient to be treated. Administration of a modified mRNA encoding the at least one biologically active peptide or polypeptide or a composition thereof to such a patient, therefore, at least partially restores the expression and/or activity of the at least one biologically active peptide or polypeptide in the patient and thereby complements the patient's genetic defect. The direct introduction of a normal, functional gene into a living animal has been studied as a means for replacing defective genetic information. In such studies, nucleic acid sequences are introduced directly into cells of a living animal. Accordingly, examples of polypeptides coded by a modified mRNA of the invention include, without limitation, dystrophin, the chloride channel, which is defectively altered in cystic fibrosis, enzymes that are lacking or defective in metabolic disorders such as phenylketonuria, galactosaemia, homocystinuria, adenosine deaminase deficiency etc.; as well as enzymes that are involved in the synthesis of neurotransmitters such as dopamine, norepinephrine and GABA, in particular tyrosine hydroxylase and DOPA decarboxylase, and alfa-1-antitrypsin etc. Pharmaceutical compositions of the invention may also be used to effect expression of cell surface receptors an/or binding partners of cell surface receptors of the modified mRNA contained therein encodes for such biologically active proteins or peptides. Examples of such proteins that in an extracellular manner or that bind to cell surface receptors include for example tissue plasminogen activator (TPA), growth hormones, insulin, interferons, granulocyte-macrophage colony stimulation factor (GM-CFS) and erythropoietin (EPO) etc.

By choosing suitable growth factors, the pharmaceutical composition of the present invention may, for example, be used for tissue regeneration or for interacting with stem cells. In this way diseases that are for example characterised by tissue degeneration, among which neurodegenerative diseases such as Alzheimer's disease, Parkinson's disease, etc. and other degenerative conditions, such as arthrosis, can be treated. In these cases the modified mRNA, in particular that contained in the pharmaceutical composition of the present invention, preferably encodes without limitation, a TGF-Beta family member, neurotrophic factors such as NGF, neurotrophines etc.

Method Of Treatment

The present invention thus further provides a method for the prevention and/or treatment of at least one disease or disorder selected from the non-limiting list comprising cancer, allergy and infectious diseases such as bacterial, viral or fungal infections, e.g. HIV infection or hepatitis.

The terms "cancer" and/or "tumor" used throughout the description are not intended to be limited to the types of cancer or tumors that may have been exemplified. The term therefore encompasses all proliferative disorders such as neoplasma, dysplasia, premalignant or precancerous lesions, abnormal cell growths, benign tumors, malignant tumors, cancer or metastasis, wherein the cancer is selected from the group of: leukemia, non-small cell lung cancer, small cell lung cancer, CNS cancer, melanoma, ovarian cancer, kidney cancer, prostate cancer, breast cancer, glioma, colon cancer, bladder cancer, sarcoma, pancreatic cancer, colorectal cancer, head and neck cancer, liver cancer, bone cancer, bone marrow cancer, stomach cancer, duodenum cancer, oesophageal cancer, thyroid cancer, hematological cancer, and lymphoma. Specific antigens for cancer can e.g. be MelanA/MART1. Cancer-germline antigens, gplOO, Tyrosinase, CEA, PSA, Her-2/neu, survivin, telomerase.

The term "infectious disease" or "infection" used throughout the description is not intended to be limited to the types of infections that may have been exemplified herein. The term therefore encompasses all infectious agents to which vaccination would be beneficial to the subject. Non-limiting examples are the following virus-caused infections or disorders: Acquired Immunodeficiency Syndrome-Adenoviridae Infections-Alphavirus Infections-Arbovirus Infections-Bell Palsy-Borna Disease-Bunyaviridae Infections-Caliciviridae Infections-Chickenpox-Common Cold-Condyloma Acuminata-Coronaviridae Infections-Coxsackievirus Infections-Cytomegalovirus Infections-Dengue-DNA Virus Infections-Contagious Ecthyma,-Encephalitis-Encephalitis, Arbovirus-Encephalitis, Herpes Simplex-Epstein-Barr Virus Infections-Erythema Infectiosum-Exanthema Subitum-Fatigue Syndrome, Chronic-Hantavirus Infections-Hemorrhagic Fevers, Viral-Hepatitis, Viral, Human-Herpes Labialis-Herpes Simplex-Herpes Zoster-Herpes Zoster Oticus-Herpesviridae Infections-HIV Infections-Infectious Mononucleosis-Influenza in Birds-Influenza, Human-Lassa Fever-Measles-Meningitis, Viral-Molluscum Contagiosum-Monkeypox-Mumps-Myelitis-Papillomavirus Infections-Paramyxoviridae Infections-Phlebotomus Fever-Poliomyelitis-Polyomavirus Infections-Postpoliomyelitis Syndrome-Rabies-Respiratory Syncytial Virus Infections-Rift Valley Fever-RNA Virus Infections-Rubella-Severe Acute Respiratory Syndrome-Slow Virus Diseases-Smallpox-Subacute Sclerosing Panencephalitis-Tick-Borne Diseases-Tumor Virus Infections-Warts-West Nile Fever-Virus Diseases-Yellow Fever-Zoonoses-Etc. Specific antigens for viruses can be HIV-gag, -tat, -rev or -nef, or Hepatitis C-antigens.

Further non-limiting examples are the following bacteria- or fungus-caused infections or disorders: Abscess-Actinomycosis-Anaplasmosis-Anthrax-Arthritis, Reactive-Aspergillosis-Bacteremia-Bacterial Infections and Mycoses-Bartonella Infections-Botulism-Brain Abscess-Brucellosis-Burkholderia Infections-*Campylobacter* Infections-Candidiasis-Candidiasis, Vulvovaginal-Cat-Scratch Disease-Cellulitis-Central Nervous System Infections-Chancroid-Chlamydia Infections-Chlamydiaceae Infections-Cholera-Clostridium Infections-Coccidioidomycosis-Corneal Ulcer-Cross Infection-Cryptococcosis-Dermatomycoses-Diphtheria-Ehrlichiosis-Empyema, Pleural-Endocarditis, Bacterial-Endophthalmitis-Enterocolitis, Pseudomembranous-Erysipelas-*Escherichia coli* Infections-Fasciitis, Necrotizing-Fournier Gangrene-Furunculosis-Fusobacterium Infections-Gas Gangrene-Gonorrhea-Gram-Negative Bacterial Infections-Gram-Positive Bacterial Infections-Granuloma Inguinale-Hidradenitis Suppurativa-Histoplasmosis-Hordeolum-Impetigo-*Klebsiella* Infections-Legionellosis-Leprosy-Leptospirosis-Listeria Infections-Ludwig-Angina-Lung Abscess-Lyme Disease-Lymphogranuloma Venereum-Maduromycosis-Melioidosis-Meningitis, Bacterial-Mycobacterium Infections-Mycoplasma Infections-Mycoses-Nocardia Infections-Onychomycosis-Osteomyelitis-Paronychia-Pelvic Inflammatory Disease-Plague-Pneumococcal Infections-Pseudomonas Infections-Psittacosis-Puerperal Infection-Q Fever-Rat-Bite Fever-Relapsing Fever-Respiratory Tract Infections-Retropharyngeal Abscess-Rheumatic Fever-Rhinoscleroma-Rickettsia Infections-Rocky Mountain Spotted Fever-Salmonella Infections-Scarlet Fever-Scrub Typhus-Sepsis-Sexually Transmitted Diseases, Bacterial-Sexually Transmitted Diseases, Bacterial-Shock, Septic-Skin Diseases, Bacterial-Skin Diseases, Infectious-Staphylococcal Infections-Streptococcal Infections-Syphilis-Syphilis, Congenital-Tetanus-Tick-Borne Diseases-Tinea-Tinea Versicolor-Trachoma-Tuberculosis-Tuberculosis, Spinal-Tularemia-Typhoid Fever-Typhus, Epidemic Louse-Borne-Urinary Tract Infections-Whipple Disease-Whooping Cough-Vibrio Infections-Yaws-Yersinia Infections-Zoonoses-Zygomycosis-Etc.

As used herein and unless otherwise stated, the term "solvate" includes any combination which may be formed by the RNA molecule(s) of this invention with a suitable inorganic solvent (e.g. hydrates) or organic solvent, such as but not limited to water for injection, hartmann's solution, PBS, 0,9% NaCl, serum free culture medium Generally, for pharmaceutical use, the RNA molecule(s) of the invention may be formulated as a pharmaceutical preparation or pharmaceutical composition comprising at least one RNA molecule of the invention and at least one pharmaceutically acceptable carrier, diluent or excipient and/or adjuvant, and optionally one or more further pharmaceutically active products.

By means of non-limiting examples, such a formulation may be in a form suitable for oral administration, for parenteral administration (such as by intralymphatic, intratumoral, intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. Nos. 6,372,778, 6,369,086, 6,369,087 and 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the products of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active product(s) contained therein, for example using liposomes or hydrophilic polymeric matrices based on natural gels or synthetic polymers. In order to enhance the solubility and/or the stability of the products of a pharmaceutical composition according to the invention, it can be advantageous to employ α-, β- or γ-cyclodextrins or their derivatives.

More in particular, the compositions may be formulated in a pharmaceutical formulation comprising a therapeutically effective amount of particles consisting of a solid dispersion of the products of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the products in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the products according to the invention involves a pharmaceutical composition whereby the products are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing at least one product according to the invention with the one or more pharmaceutically acceptable carriers, and, if desired, in combination with other pharmaceutical active products, when necessary under aseptic conditions. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0,1 and 1000 mg.

The products can be administered by a variety of routes including the intralymphatic, intratumoral, oral, rectal, ocular, transdermal, subcutaneous, intravenous, intramuscular or intranasal routes, depending mainly on the specific preparation used and the condition to be treated or prevented. The at least one product of the invention will generally be administered in an "effective amount", by which is meant any amount of a product that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the products of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the product according to the invention, if desired with the substances customary therefore such as solubilizers, emulsifiers or further auxiliaries are brought into solution, suspension, or emulsion. The products of the invention can also be lyophilized and the lyophilizates obtained used, for example, for the production of injection or infusion preparations. Suitable solvents are, for example, water, physiological saline solution in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the products according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the products and compositions of the invention are used locally, for instance topical or in both absorbed and non-adsorbed applications.

The compositions are of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a composition for veterinary use that contains at least one product of the invention and at least one suitable carrier (i.e. a carrier suitable for veterinary use). The invention also relates to the use of a product of the invention in the preparation of such a composition.

EXAMPLES

General Material and Methods

In Vitro Experiments: Generation of Monocyte derived DCs

Peripheral blood mononuclear cells (PBMC) were used as a source of DC precursors and isolated from leukapheresis products. Clinical grade DCs were generated in vitro from the plastic adherent fraction as follows. On day 0, PBMC were plated at a density of $10 \times 10^6$ cells/mL in medium suitable for haematopoietic cell culture supplemented with 2% autologous plasma (AP). The cells were left for 2 h to allow plastic adherence of the monocytes at 37° C.

Non-adherent cells were removed by washing, and the adherent cells were cultured in medium supplemented with 1% AP, 1,000 U/mL GM-CSF and 500 U/mL IL-4 in the Cell Factory. On day 2 and 4, medium containing the cytokine amount of day 0 was added to the DC culture. On day 6 of DC culture, the cells were harvested and cryopreserved.

In Vitro Experiments: Electroporation of DCs

On day 6, 4-8×10$^6$ DCs were electroporated with mRNA as indicated. Before electroporation, the DCs were washed twice, first with PBS without supplements and secondly with reduced serum medium without phenol red. After the second wash step, the DCs were resuspended in a final volume of 200 µl of reduced serum medium containing the mRNA. Electroporation was performed in a 4-mm gap electroporation cuvette. An exponential decay pulse was used with the following conditions: voltage, 300V; capacitance, 150 µF, and resistance, $\infty\Omega$, resulting in a pulse time of ≈11 ms. Immediately after electroporation, the DCs were diluted in medium supplemented with 1% huAB serum and PS/L-GLU and incubated at 37° C. in a humidified 5% $CO_2$ atmosphere. No additional cytokines were added to the DCs after electroporation.

In Vivo Experiments: Mice

Female, 6 to 12 weeks old DBA/2 mice.

In Vivo Experiments: Mouse Cell Lines

The mastocytoma cell line P815 was obtained from C. Uyttenhove (Universite Catholique de Louvain, Louvain-La-Neuve, Belgium).

In Vivo Experiments: Tumor Cell Inoculation and In Situ Delivery of mRNA

In order to grow palpable tumors, mice were injected with 5×10$^5$ P815 tumor cells subcutaneously at both flanks as indicated in the experiment. For intratumoral delivery of mRNA, mice were anesthetized with Isoflurane (Abbott). Tumors were injected with a mixture containing 10 µg of each TriMix mRNA component in a final volume of 50 µl 0.8 Hartmann's solution/injected tumor when they reached a volume of about 100 mm$^3$. The same amount of mRNA was used between the different groups. mRNA encoding tNGFR produced from a pGEM vector served as a control.

Example 1

Specific Material and Methods iDCs generation and electroporation are performed as described in the general material and methods part above. iDCs were electroporated with 5 µg of each component of TriMix to allow maturation of the DCs. All flow cytometric stainings were performed in PBS/BSA/azide. To analyze the expression of CD70, anti CD70-fluorescein isothiocyanate (FITC) was used. Data acquisition was performed on a FACSFortessa flow cytometer (BD) and analyzed using FACS Diva software.

Figure 1:
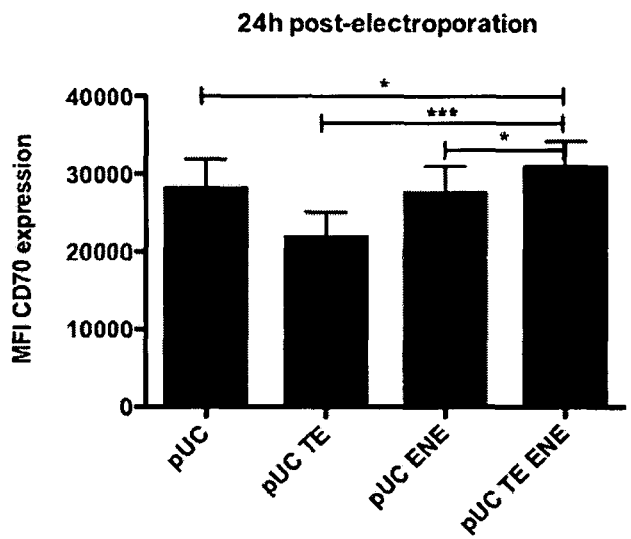
FIG. 1: iDCs were electroporated with TriMix mRNA encoded by the pUC-vector, the pUC-TE vector, pUC-ENE vector or the pUC TE ENE-vector. MFI (mean fluorescence intensity) values of the positive DC population are shown. Data are presented as mean±SEM. (Paired t test, *P<0.05). N pUC=6; N pUC-TE=15; N pUC-ENE=15; N pUC TE ENE=19

Result:

Twenty-four hours after electroporation, DCs were stained for their CD70 surface expression. These results show that after electroporation of iDCs with TriMix, the intensity of CD70 expression-mean fluorescence intensity (MFI)-is significantly higher after electroporation with Tri-Mix encoded by the pUC TE ENE plasmid (SEQ ID No 5) containing both regulatory elements (TE+ENE), when compared to the pUC-vector (basis of the pUC TE ENE plasmid), the pUC TE-vector and the pUC ENE-vector. CD70 expression after electroporation with TriMix encoded by the pUC TE ENE plasmid is significantly higher, whereas both the use of pUC TE and pUC ENE result in a reduced or at maximum equal levels of CD70 expression compared to pUC lacking these elements (FIG. 1). Hence, the presence of both elements (TE and ENE) in the vector appear to have an unexpected synergistic effect in terms of increasing CD70 expression after electroporation with TriMix encoded by the pUC TE ENE plasmid.

Example 2

Specific Material & Methods iDCs generation and electroporation conditions are performed as described in the general material and methods part above. iDCs were electroporated with 20 µg WT1 encoding mRNA to allow antigen loading. To analyze intracellular WT1 expression, cells were fixed and permeabilized, and stained intracellularly with an anti-WT1 monoclonal antibody (clone 6F-H2; Dako Cytomation, Carpinteria, Calif.). An IgG isotype-matched PE-labeled anti-mouse antibody was used as secondary Ab (Becton & Dickinson, Erembodegem, Belgium). Non-reactive isotype-matched antibody (eBioscience, Vienna, Austria) was used as control. Data acquisition was performed on a FACSFortessa flow cytometer (BD) and analyzed using FACS Diva software.

Result:

These results show that after electroporation of iDC with WT1 encoded by the pUC TE ENE-vector, a more prolonged WT1 expression is observed when compared to the other WT1 mRNA-encoding vectors (FIGS. 2A-2C). These data nicely demonstrate the different ways of action of both 5'TE and 3'ENE segments. While the expression of mRNA from the pUC-TE vector is high after 4 hours, it deteriorates rapidly. Translation from the ENE containing RNA is lower than all others during the entire period. The pUC TE ENE-vector has the high translatability of the TE and the long-lived effect of the ENE sequence. The expression level of WT1 diminishes at a significantly slower rate than in the other vectors.

Example 3

Specific Material & Methods:

iDCs generation and electroporation conditions are performed as described in the general material and methods part above. iDCs were co-electroporated with 5µg eGFP encoding mRNA and TriMix (5µg of each component) to allow antigen loading and maturation of the DCs. eGFP expression was assessed by flow cytometry at several time points.

Result:

eGFP expression was followed-up at several time points after electroporation (FIG. 3). These results show that the expression level of eGFP from both vectors is comparable 4 hours after electroporation. However on later time points it is clear that expression from pUC TE ENE derived mRNA is significantly higher. Again this points at a more stable and prolonged expression of the transgene.

Example 4

Specific Material & Methods:

iDCs generation and electroporation conditions are performed as described above. iDCs were electroporated with 5pg of each component of TriMix to allow maturation of the DCs. All flow cytometric stainings were performed in PBS/BSA/azide. To analyze the expression of surface molecules on the cell surface of the DCs, the following monoclonal antibodies were used: CD40-APC (Allophycocyanin), CD70-FITC, CD80-PE, CD83-PE (Phycoerythrin), CD86-PE and CCR7-APC. Data acquisition was performed on a FACS Fortessa flow cytometer (BD) and analyzed using FACS Diva software.

Result:

Electroporation of iDCs with TriMix mRNA encoded by the pUC TE ENE-vector is able to induce maturation of the DCs (FIGS. 4A-4E).

Example 5

Two-side Tumor Model With P815: Single Treatment of One Tumor

Specific Material & Methods:

In order to grow palpable tumors, mice were inoculated with $5\times10^5$ P815 tumor cells subcutaneously at both flanks. Therapy was started when both tumors reached an injectable volume of about 100 mm³. By using a two-side tumor model in which only one tumor was treated, we aimed to evaluate the systemic effect of the vaccination strategy. Therefore, only the left tumor was injected with either control mRNA or pUC TE ENE TriMix mRNA (10 µg of each mRNA component) dissolved in 0.8×Hartmann's solution. The systemic anti-tumor immune response was evaluated by measuring the size of both treated and non-treated, contralateral tumor and by survival.

Result:

By using a two-side tumor model, we could evaluate the systemic effect of the immunization strategy. Single intratumoral delivery of pUC TE ENE TriMix mRNA resulted in a significantly reduced tumor growth of both treated and non-treated contralateral tumor (FIGS. 5A-5F). The effect of vaccination on the distant tumor could be an indication that a single intratumoral TriMix injection could be used to treat multiple tumor lesions.

Example 6

Two-side Tumor Model With P815: Single Treatment of One Tumor, Hartmann Solution and tNGFR as Control Specific Material & Methods:

In order to grow palpable tumors, mice were inoculated with $5\times10^5$ P815 tumor cells subcutaneously at both flanks. Therapy was started when both tumors reached an injectable volume of about 100 mm³. By using a two-side tumor model by which only one tumor was treated, we aimed to evaluate the systemic effect of the vaccination strategy. Therefore, only the left tumor was injected with either Vehicle (0.8 Hartmann's solution), control mRNA or pUC TE ENE TriMix mRNA (10 µg of each mRNA component) dissolved in 0.8×Hartmann's solution, all in a total volume of 50 µl/injected tumor. The systemic anti-tumor immune response was evaluated by measuring the size of both treated and non-treated, contralateral tumor and by survival.

Result:

By using a two-side tumor model, we could evaluate the systemic effect of the immunization strategy. This experiment confirms the previous observations, i.e.

1. Single intratumoral delivery of pUC TE ENE TriMix mRNA resulted in a significantly reduced tumor growth of both treated and non-treated contralateral tumor.
2. Single intratumoral delivery of pUC TE ENE TriMix mRNA resulted in a prolonged survival of tumor-bearing mice
3. The effect of vaccination was more pronounced on treated tumors.

Additionally, by taking along a group by which tumors were treated with vehicle, we could show the adjuvant effect of mRNA itself.

Example 7

Comparison of Different TE Sequences

Specific Material & Methods:

Details regarding the specific assay methods in relation hereto may be found in examples 2 and 3 as described above.

Result: Electroporation of iDC With WT1 or eGFP

Electroporation of iDC with WT1 (FIG. 9A) or eGFP (FIG. 9B) encoded by the pUC TE ENE-vectors either comprising a TE element represented by SEQ ID No1, SEQ ID No2 or SEQ ID No3 did not result in a significant difference of WT1 or eGFP expression respectively.

These data clearly indicate that sequences having at least 80% sequence identity to SEQ ID No1, such as for example SEQ ID No1, SEQ ID No2 or SEQ ID No3, could be used interchangeably as the translation enhancer element in the vectors according to this invention.

REFERENCES

Bonehill A, Tuyaerts S, Van Nuffel A M, Heirman C, Bos T J, Fostier K, Neyns B, Thielemans K—*Enhancing the T-cell stimulatory capacity of human dendritic cells by co-electroporation with CD40L, CD70 and constitutively active TLR4 encoding mRNA.*—Mol Ther. 2008 June; 16(6):1170-80.

Conrad N K, Steitz J A—*A Kaposi's sarcoma virus RNA element that increases the nuclear abundance of intronless transcripts.*—EMBO J. 2005 May 18; 24(10):1831-41.

Conrad N K, Mili S, Marshall E L, Shu M D, Steitz J A—*Identification of a rapid mammalian deadenylation-dependent decay pathway and its inhibition by a viral RNA element.* Mol Cell. 2006; 24:943-953.

Diken M, Kreiter S, Selmi A, Britten C M, Huber C, Türeci Ö, Sahin U—*Selective uptake of naked vaccine RNA by dendritic cells is driven by macropinocytosis and abrogated upon DC maturation.*—Gene Ther. 2011 July; 18(7):702-8.

Fotin-Mleczek M, Duchardt K M, Lorenz C, Pfeiffer R, Ojkić-Zma S, Probst J, Kallen K J—*Messenger RNA-based vaccines with dual activity induce balanced TLR-7 dependent adaptive immune responses and provide antitumor activity.*—J Immunother. 2011 January; 34(1):1-15.

Hu M C, Tranque P, Edelman G M, Mauro V P.—*rRNA-complementarity in the 5' untranslated region of mRNA specifying the Gtx homeodomain protein: evidence that base-pairing to 18S rRNA affects translational efficiency.*—Proc Natl Acad Sci USA. 1999 Feb. 16; 96(4): 1339-44.

Mitton-Fry R M, DeGregorio S J, Wang J, Steitz T A, Steitz J A.—*Poly(A) tail recognition by a viral RNA element through assembly of a triple helix.*—Science. 2010; 330: 1244-1247.

Sun R, Lin S F, Gradoville L, Miller G.—*Polyadenylylated nuclear RNA encoded by Kaposi sarcoma-associated herpesvirus.*—Proc Natl Acad Sci USA. 1996; 93:11883-11888.

Van Lint Sandra, Goyvaerts Cleo, Maenhout Sarah, et al.—*Preclinical Evaluation of TriMix and Antigen mRNA Based Antitumor Therapy*—Cancer Res 2012; 72:1661-1671.

The invention claimed is:

1. A nucleic acid vector comprising a translation enhancer (TE) sequence which is 89% identical to the nucleotide sequence set forth in SEQ ID NO: 1, a transcribable nucleic acid sequence and a nuclear retention sequence which is identical to the nucleotide sequence set forth in SEQ ID NO: 4.

2. The nucleic acid vector according to claim 1, wherein said transcribable nucleic acid sequence is selected from the mRNA encoding CD40L, CD70, caTLR4 or antigen/disease-specific mRNA.

3. The nucleic acid vector according to claim 1, wherein said translation enhancer is identical to the nucleotide sequence set forth in SEQ ID NO: 1.

4. An in vitro method of increasing stability and/or translation efficiency of transcribed RNA; said method comprising:
   i) providing a vector according to claim 1, wherein said transcribable nucleic acid sequence is a transcribable DNA sequence, which corresponds to said RNA to be transcribed; and
   (ii) transcribing in vitro said transcribable DNA sequence.

5. A kit comprising one or more vectors according to claim 1.

* * * * *

UNITED STATES PATENT AND TRADEMARK OFFICE
CERTIFICATE OF CORRECTION

| | |
|---|---|
| PATENT NO. | : 10,159,755 B2 |
| APPLICATION NO. | : 15/034048 |
| DATED | : December 25, 2018 |
| INVENTOR(S) | : Carlo Heirman and Kristiaan Thielemans |

Page 1 of 1

It is certified that error appears in the above-identified patent and that said Letters Patent is hereby corrected as shown below:

In the Specification

Column 8, Line 55:
"associate to both the poly-A tail and the e1F4 complex on the"
Should read:
--associate to both the poly-A tail and the elF4 complex on the--;

Column 9, Line 41:
"comparison to SEQ ID No1, and are thus suitable to used in"
Should read:
--comparison to SEQ ID No1, and are thus suitable to be used in--;

Column 16, Line 52:
"located at a defined distance form the DNA binding site."
Should read:
--located at a defined distance from the DNA binding site.--;

Column 17, Line 53:
"surface receptors an/or binding partners of cell surface"
Should read:
--surface receptors and/or binding partners of cell surface--;

Column 24, Line 63:
"5pg of each component of TriMix to allow maturation of the"
Should read:
--5μg of each component of TriMix to allow maturation of the--.

Signed and Sealed this
Nineteenth Day of November, 2019

Andrei Iancu
*Director of the United States Patent and Trademark Office*

SEQUENCE LISTING

<160> NUMBER OF SEQ ID NOS: 5

<210> SEQ ID NO 1
<211> LENGTH: 204
<212> TYPE: DNA
<213> ORGANISM: Artificial Sequence
<220> FEATURE:
<221> NAME/KEY: source
<222> LOCATION: 1..204
<223> OTHER INFORMATION: /organism="Artificial Sequence"
      /note="Translation Enhancer"
      /mol_type="unassigned DNA"

<400> SEQUENCE: 1
ggccggcggg tttctgacat ccggcgggtt tctgacatcc ggcgggtttc tgacatccgg    60
cgggtttctg acatccggcg ggtgaattct tctgacatcc ggcgggtttc tgacatccgg   120
cgggtttctg acatccggcg ggtttctgac atccggcggg tttctgacat ccggcgggtg   180
actcacaacc aggcctccac aacc                                          204

<210> SEQ ID NO 2
<211> LENGTH: 238
<212> TYPE: DNA
<213> ORGANISM: Artificial Sequence
<220> FEATURE:
<221> NAME/KEY: source
<222> LOCATION: 1..238
<223> OTHER INFORMATION: /organism="Artificial Sequence"
      /note="Translation Enhancer"
      /mol_type="unassigned DNA"

<400> SEQUENCE: 2
aagctttaat acgactcact atagggccgg cgggtttctg acatccggcg ggtttctgac    60
atccggcggg tttctgacat ccggcgggtt tctgacatcc ggcgggtttc tgacatccgg   120
cgggtttctg acatccggcg ggtttctgac atccggcggg tttctgacat ccggcgggtt   180
tctgacatcc ggcgggtttc tgacattcac aaccaggcct ccacaaccat ggctcgag    238

<210> SEQ ID NO 3
<211> LENGTH: 238
<212> TYPE: DNA
<213> ORGANISM: Artificial Sequence
<220> FEATURE:
<221> NAME/KEY: source
<222> LOCATION: 1..238
<223> OTHER INFORMATION: /organism="Artificial Sequence"
      /note="Translation Enhancer"
      /mol_type="unassigned DNA"

<400> SEQUENCE: 3
aagctttaat acgactcact atagggccgg cggaattctg acatccggcg gaattctgac    60
atccggcgga attctgacat ccggcggaat tctgacatcc ggcggaattc tgacatccgg   120
cggaattctg acatccggcg gaattctgac atccggcgga attctgacat ccggcggaat   180
tctgacatcc ggcggaattc tgacattcac aaccaggcct ccacaaccat ggctcgag    238

<210> SEQ ID NO 4
<211> LENGTH: 85
<212> TYPE: DNA
<213> ORGANISM: Artificial Sequence
<220> FEATURE:
<221> NAME/KEY: source
<222> LOCATION: 1..85
<223> OTHER INFORMATION: /organism="Artificial Sequence"
      /note="Nuclear Retention Element"
      /mol_type="unassigned DNA"

```
<400> SEQUENCE: 4
tcgagtgttt tggctgggtt tttccttgtt cgcaccggac acctccagtg accagacggc    60
aaggttttta tcccagtgta tattg                                          85

<210> SEQ ID NO 5
<211> LENGTH: 3102
<212> TYPE: DNA
<213> ORGANISM: Artificial Sequence
<220> FEATURE:
<221> NAME/KEY: source
<222> LOCATION: 1..3102
<223> OTHER INFORMATION: /organism="Artificial Sequence"
      /note="Empty pUC TE ENE vector"
      /mol_type="unassigned DNA"

<400> SEQUENCE: 5
taatacgact cactataggg ccggcgggtt tctgacatcc ggcgggtttc tgacatccgg    60
cgggtttctg acatccggcg gtttctgac atccggcggg tttctgacat ccggcgggtt   120
tctgacatcc ggcgggtttc tgacatccgg cgggtttctg acatccggcg gtttctgac   180 atccggcggg tttctgacat tcacaaccag gcctccacaa ccctcgagtg ttttggctgg   240 gttttttcctt gttcgcaccg gacacctcca gtgaccagac ggcaaggttt tatcccagt   300 gtatattgtc gacaaaaaaa aaaaaaaaaa aaaaaaaaaa aaaaaaaaaa aaaaaaaaaa   360
aaaaaaaaaa aaaaaaaaaa aaaaaaaaaa aaaaaaaaaa aaaaaaaaaa aaaaaaaaaa   420
aaaaaaaaaa aaaaaaagca ggtgtgtctc tctccacctg cgaattcact ggccgtcgtt   480
ttacaacgtc gtgactggga aaccctggcg ttacccaac ttaatcgcct tgcagcacat   540 cccccttcg ccagctggcg taatagcgaa gaggcccgca ccgatcgccc ttcccaacag   600
ttgcgcagcc tgaatggcga atggcgcctg atgcggtatt ttctccttac gcatctgtgc   660
ggtatttcac accgcatatg gtgcactctc agtacaatct gctctgatgc cgcatagtta   720
agccagcccc gacacccgcc aacacccgct gacgcgccct gacgggcttg tctgctcccg   780
gcatccgctt acagacaagc tgtgaccgtc tccgggagct gcatgtgtca gaggttttca   840
ccgtcatcac cgaaacgcgc gagacgaaag gcctcgtga tacgcctatt tttataggtt   900
aatgtcatga taataatggt ttcttagacg tcaggtggca cttttcgggg aaatgtgcgc   960
ggaacccctA tttgtttatt tttctaaata cattcaaata tgtatccgct catgagacaa  1020
taaccctgat aaatgcttca ataatattga aaaggaaga gtatgagtat tcaacatttc  1080
cgtgtcgccc ttattccctt ttttgcggca ttttgccttc ctgttttgc tcacccagaa  1140 acgctggtga agtaaaaga tgctgaagat cagttgggtg cacgagtggg ttacatcgaa  1200
ctggatctca acagcggtaa gatccttgag agttttcgcc ccgaagaacg ttttccaatg  1260
atgagcactt ttaaagttct gctatgtggc gcggtattat cccgtattga cgccgggcaa  1320
gagcaactcg gtcgccgcat acactattct cagaatgact tggttgagta ctcaccagtc  1380
acagaaaagc atcttacgga tggcatgaca gtaagagaat tatgcagtgc tgccataacc  1440
atgagtgata acactgcggc caacttactt ctgacaacga tcggaggacc gaaggagcta  1500
accgcttttt tgcacaacat gggggatcat gtaactcgcc ttgatcgttg ggaaccggag  1560
ctgaatgaag ccataccaaa cgacgagcgt gacaccacga tgcctgtagc aatggcaaca  1620
acgttgcgca aactattaac tggcgaacta cttactctag cttcccggca acaattaata  1680
gactggatgg aggcggataa agttgcagga ccacttctgc gctcggccct tccggctggc  1740
tggtttattg ctgataaatc tggagccggt gagcgtgggt ctcgcggtat cattgcagca  1800
```

-continued

```
ctggggccag atggtaagcc ctcccgtatc gtagttatct acacgacggg gagtcaggca    1860
actatggatg aacgaaatag acagatcgct gagataggtg cctcactgat taagcattgg    1920
taactgtcag accaagttta ctcatatata ctttagattg atttaaaact tcatttttaa    1980
tttaaaagga tctaggtgaa gatccttttt gataatctca tgaccaaaat cccttaacgt    2040
gagttttcgt tccactgagc gtcagacccc gtagaaaaga tcaaaggatc ttcttgagat    2100 ccttttttc tgcgcgtaat ctgctgcttg caaacaaaaa aaccaccgct accagcggtg     2160
gtttgtttgc cggatcaaga gctaccaact cttttccga aggtaactgg cttcagcaga     2220
gcgcagatac caaatactgt tcttctagtg tagccgtagt taggccacca cttcaagaac    2280
tctgtagcac cgcctacata cctcgctctg ctaatcctgt taccagtggc tgctgccagt    2340
ggcgataagt cgtgtcttac cgggttggac tcaagacgat agttaccgga taaggcgcag    2400
cggtcgggct gaacggggggg ttcgtgcaca cagcccagct tggagcgaac gacctacacc   2460
gaactgagat acctacagcg tgagctatga gaaagcgcca cgcttcccga agggagaaag    2520
gcggacaggt atccggtaag cggcagggtc ggaacaggag agcgcacgag ggagcttcca    2580 ggggggaaacg cctggtatct ttatagtcct gtcgggtttc gccacctctg acttgagcgt   2640
cgatttttgt gatgctcgtc aggggggcgg agcctatgga aaaacgccag caacgcggcc   2700
tttttacggt tcctggcctt ttgctggcct tttgctcaca tgttctttcc tgcgttatcc    2760
cctgattctg tggataaccg tattaccgcc tttgagtgag ctgataccgc tcgccgcagc    2820
cgaacgaccg agcgcagcga gtcagtgagc gaggaagcgg aagagcgccc aatacgcaaa    2880
ccgcctctcc ccgcgcgttg gccgattcat taatgcagct ggcacgacag gtttcccgac    2940
tggaaagcgg gcagtgagcg caacgcaatt aatgtgagtt agctcactca ttaggcaccc    3000
caggctttac actttatgct tccggctcgt atgttgtgtg gaattgtgag cggataacaa    3060
tttcacacag gaaacagcta tgaccatgat tacgccaagc tt                       3102
```